(12) United States Patent
Carr

(10) Patent No.: US 12,718,940 B2
(45) Date of Patent: Aug. 25, 2026

(54) HANDSFREE COMMUNICATION SYSTEM AND METHOD

(71) Applicant: Kevin Carr, Milford, CT (US)

(72) Inventor: Kevin Carr, Milford, CT (US)

(73) Assignee: EDERA L3C, Washington, DC (US)

( * ) Notice: Subject to any disclaimer, the term of this patent is extended or adjusted under 35 U.S.C. 154(b) by 69 days.

(21) Appl. No.: 17/874,723

(22) Filed: Jul. 27, 2022

(65) Prior Publication Data

US 2023/0031353 A1 Feb. 2, 2023

Related U.S. Application Data

(60) Provisional application No. 63/226,708, filed on Jul. 28, 2021.

(51) Int. Cl.
*G16H 40/67* (2018.01)
*A61B 5/00* (2006.01)
(Continued)

(52) U.S. Cl.
CPC ............. *G16H 40/67* (2018.01); *A61B 5/165* (2013.01); *A61B 5/4803* (2013.01); *G06F 9/453* (2018.02); *G06F 40/40* (2020.01); *G10L 15/02* (2013.01); *G10L 15/08* (2013.01); *G10L 15/1807* (2013.01); *G10L 15/183* (2013.01); *G10L 15/22* (2013.01); *G10L 15/26* (2013.01); *G10L 25/63* (2013.01); *G16H 10/20* (2018.01); *G16H 20/10* (2018.01); *G16H 20/70* (2018.01);
(Continued)

(58) Field of Classification Search
CPC .............. G16H 40/67; G06Q 50/20–26; G10L 2015/223; G06F 9/453
USPC ........................................................ 705/2, 3
See application file for complete search history.

(56) References Cited

U.S. PATENT DOCUMENTS 5,335,313 A * 8/1994 Douglas .................. G10L 15/26
704/E15.045
5,592,153 A 1/1997 Welling et al.
(Continued)

FOREIGN PATENT DOCUMENTS

CN 111918618 A 11/2020
EP 3796324 A1 * 3/2021 ............. G06F 21/32
(Continued)

OTHER PUBLICATIONS

G. Nagy et al., "An Anytime Voice Controlled Ambient Assisted Living System for motion disabled persons," 2015 IEEE International Symposium on Medical Measurements and Applications (MeMeA) Proceedings, Turin, Italy, 2015, pp. 163-168, doi: 10.1109/MeMeA.2015.7145192. (Year: 2015).*
(Continued)

*Primary Examiner* — Christopher L Gilligan
*Assistant Examiner* — Jessica Marie Webb
(74) *Attorney, Agent, or Firm* — Brian J. Colandreo; Heath M. Sargeant; Holland & Knight LLP

(57) ABSTRACT

A method, computer program product, and computing system for monitoring the diction of a patient within a hospital room; processing at least a portion of the diction to identify at least one bed-control-command to be performed on a hospital bed within the hospital room; and if at least one bed-control-command is detected, effectuating the at least one bed-control-command on the hospital bed within the hospital room.

24 Claims, 10 Drawing Sheets

(51) Int. Cl.

| | |
|---|---|
| ***A61B 5/16*** | (2006.01) |
| ***G06F 9/451*** | (2018.01) |
| ***G06F 40/40*** | (2020.01) |
| ***G10L 15/02*** | (2006.01) |
| ***G10L 15/08*** | (2006.01) |
| ***G10L 15/18*** | (2013.01) |
| ***G10L 15/183*** | (2013.01) |
| ***G10L 15/22*** | (2006.01) |
| ***G10L 15/26*** | (2006.01) |
| ***G10L 25/63*** | (2013.01) |
| ***G16H 10/20*** | (2018.01) |
| ***G16H 20/10*** | (2018.01) |
| ***G16H 20/70*** | (2018.01) |
| ***G16H 40/20*** | (2018.01) |
| ***G16H 40/63*** | (2018.01) |
| ***G16H 70/20*** | (2018.01) |
| ***G16H 80/00*** | (2018.01) |
| ***H04L 51/02*** | (2022.01) |
| *A61G 7/018* | (2006.01) |
| *G06Q 10/10* | (2023.01) |

(52) U.S. Cl.

CPC ............. *G16H 40/20* (2018.01); *G16H 40/63* (2018.01); *G16H 70/20* (2018.01); *G16H 80/00* (2018.01); *H04L 51/02* (2013.01); *A61G 7/018* (2013.01); *G06Q 10/10* (2013.01); *G10L 2015/088* (2013.01)

(56) References Cited

U.S. PATENT DOCUMENTS 6,131,868 A 10/2000 Welling et al.
6,273,975 B1 8/2001 Van Der Meulen
6,278,975 B1 8/2001 Brant et al.
6,761,344 B2 7/2004 Welling et al.
8,959,030 B2 2/2015 Ricci
10,366,784 B1 7/2019 Eller
10,452,816 B2 10/2019 Kidd et al.
10,468,130 B1 11/2019 Taneja
10,510,348 B1 12/2019 Lavery et al.
10,573,307 B2 2/2020 Skantze et al.
10,685,329 B2 6/2020 Taylor et al.
10,811,127 B1 10/2020 Mathur et al.
10,839,153 B2 11/2020 Gaur et al.
10,896,688 B2 1/2021 Vaculin et al.
10,930,273 B2 2/2021 Cheng et al.
11,024,304 B1 * 6/2021 Smith ..................... G10L 15/22
11,029,918 B2 6/2021 Brown et al.
11,100,922 B1 * 8/2021 Mutagi ................... G06F 3/167
11,431,660 B1 8/2022 Leeds et al.
11,631,401 B1 4/2023 Nudd et al.
11,793,455 B1 * 10/2023 Kahn ..................... A47C 20/04
2002/0042725 A1 4/2002 Mayaud
2002/0052762 A1 5/2002 Kobylevsky et al.
2003/0230702 A1 12/2003 Welling et al.
2005/0007258 A1 1/2005 Moster et al.
2005/0165609 A1 7/2005 Zuberec et al.
2006/0029273 A1 2/2006 Lipscher et al.
2006/0224414 A1 10/2006 Astrup et al.
2007/0233498 A1 10/2007 Silverman et al.
2008/0091464 A1 4/2008 Lipscher et al.
2009/0049610 A1 * 2/2009 Heimbrock ............ A61G 7/012 704/275
2009/0271438 A1 10/2009 Agapi et al.
2010/0229102 A1 9/2010 Chriss
2010/0231421 A1 9/2010 Rawls-Meehan
2011/0202370 A1 8/2011 Green et al.
2011/0301943 A1 12/2011 Patch
2012/0046966 A1 2/2012 Chang et al.
2012/0239429 A1 9/2012 Corfield
2013/0035946 A1 * 2/2013 Ratan ..................... G16H 40/67 705/2
2013/0090927 A1 4/2013 Quatieri et al.
2013/0152092 A1 6/2013 Yadgar
2013/0297347 A1 11/2013 Cardoza et al.
2014/0019128 A1 1/2014 Riskin et al.
2014/0046926 A1 2/2014 Walton
2014/0074454 A1 * 3/2014 Brown .................... G10L 15/08 704/235
2014/0169795 A1 6/2014 Clough
2014/0249830 A1 9/2014 Gallopyn et al.
2014/0249831 A1 * 9/2014 Gallopyn ............... G16H 40/20 705/2
2014/0330586 A1 11/2014 Riskin et al.
2015/0213224 A1 7/2015 Amarasingham et al.
2015/0286858 A1 10/2015 Shaburov et al.
2016/0099011 A1 4/2016 Scherer et al.
2017/0132199 A1 5/2017 Vescovi et al.
2017/0160813 A1 6/2017 Divakaran et al.
2017/0199984 A1 * 7/2017 Lohman ................. G16H 10/20
2017/0206504 A1 7/2017 Taylor et al.
2017/0245759 A1 8/2017 Jain et al.
2017/0289350 A1 10/2017 Philbin
2017/0357774 A1 12/2017 Figg
2018/0053119 A1 2/2018 Zeng et al.
2018/0068082 A1 3/2018 Brown et al.
2018/0116415 A1 * 5/2018 Karschnik ............. A47C 27/15
2018/0137856 A1 5/2018 Gilbert
2018/0150605 A1 5/2018 Co et al.
2018/0165723 A1 6/2018 Wright et al.
2018/0240535 A1 8/2018 Harper et al.
2018/0240538 A1 8/2018 Koll et al.
2018/0263833 A1 * 9/2018 Pham ..................... A61G 9/003
2018/0277093 A1 9/2018 Carr et al.
2018/0285595 A1 10/2018 Jessen
2018/0308565 A1 10/2018 Pinter et al.
2018/0315428 A1 11/2018 Johnson et al.
2018/0342329 A1 * 11/2018 Rufo ...................... G16H 40/67
2018/0369038 A1 12/2018 Bhimavarapu et al.
2018/0375807 A1 12/2018 Krans et al.
2019/0008708 A1 1/2019 Moreno et al.
2019/0018694 A1 1/2019 Rhodes et al.
2019/0051415 A1 2/2019 Owen
2019/0065464 A1 2/2019 Finley et al.
2019/0066680 A1 2/2019 Woo et al.
2019/0074028 A1 3/2019 Howard
2019/0082224 A1 3/2019 Bradley et al.
2019/0121532 A1 4/2019 Strader et al.
2019/0122766 A1 4/2019 Strader et al.
2019/0164170 A1 5/2019 Kataria et al.
2019/0189259 A1 6/2019 Clark
2019/0205148 A1 7/2019 Schur
2019/0214121 A1 7/2019 O'Keeffe et al.
2019/0231079 A1 * 8/2019 Schulte ................ A47C 31/008
2019/0279647 A1 9/2019 Jones et al.
2019/0385711 A1 12/2019 Shriberg et al.
2020/0005783 A1 1/2020 Judy et al.
2020/0043576 A1 2/2020 Riku
2020/0082299 A1 3/2020 Vasconcelos et al.
2020/0118458 A1 4/2020 Shriberg et al.
2020/0137230 A1 4/2020 Spohrer
2020/0205580 A1 * 7/2020 Sayadi ................. A47C 27/083
2020/0221951 A1 7/2020 Amble et al.
2020/0227041 A1 * 7/2020 Tang ...................... H04R 1/028
2020/0243186 A1 7/2020 Gallopyn et al.
2020/0244605 A1 7/2020 Nagaraja et al.
2020/0286480 A1 9/2020 Singh
2020/0335187 A1 10/2020 Lefkofsky et al.
2020/0358900 A1 11/2020 Carty et al.
2020/0410983 A1 12/2020 Mohajer et al.
2021/0056976 A1 2/2021 Brown et al.
2021/0104317 A1 4/2021 Warner et al.
2021/0117479 A1 4/2021 Liu et al.
2021/0183389 A1 6/2021 Gilbert
2021/0200598 A1 7/2021 Barczyk et al.
2021/0232361 A1 7/2021 Brown et al.
2021/0256832 A1 8/2021 Weisz et al.
2021/0327423 A1 10/2021 Dudley et al.
2021/0334473 A1 10/2021 Trehan
2021/0335503 A1 10/2021 Williams et al.
2021/0352176 A1 11/2021 Van et al.

(56) References Cited

U.S. PATENT DOCUMENTS

2022/0101847 A1 3/2022 Receveur et al.
2022/0374605 A1 11/2022 Sethi et al.
2022/0391480 A1* 12/2022 Schweinfurth ......... G06F 3/167

FOREIGN PATENT DOCUMENTS

WO 2008/099290 A1 8/2008
WO 2014/169269 A1 10/2014
WO 2021081418 A1 4/2021
WO 2023/009644 A1 2/2023
WO 2023/009647 A1 2/2023
WO 2023/009650 A1 2/2023
WO 2023/009659 A1 2/2023
WO 2023/009660 A1 2/2023
WO 2023/009661 A1 2/2023
WO 2023009640 A1 2/2023

OTHER PUBLICATIONS

Fast Company, Feb. 1, 2018, “You Can Control This Bed With Your Voice | Useful/Useless”, YouTube, https://www.youtube.com/watch?v=kw00_GuH5x4 (Year: 2018).*
Diniz de Faria, Gabriel, “Smart Thermally Controlled Bedding”, 2018, IP.com, IP.com No. IPCOM000255167D, all pages, https://ip.com/IPCOM/000255167 (Year: 2018).*
(N.A.), “Ananda Adjustable Bed Frame with Pillow Tilt, Massage, USB, Alexa Voice Command”, Oct. 24, 2018, AnandaSleep, all pages. https://anandasleep.com/products/adjustable-base?srsltid=AfmBOorHIZ3o7w3loEEs7A2_EgSZIZ2VbaAvYum3hbY5VUOsEHVOVV7y (Year: 2018).*
International Search Report and Written Opinion issued on Nov. 7, 2022 in PCT Application Serial No. PCT/US2022/038575.
Lee. “How Aiva Health Is Creating New Opportunities for COVID-Safe Care.” Alexa Skills Kit. Mar. 4, 2021 (Mar. 4, 2021) Retrieved on Oct. 6, 2022 (Oct. 6, 2022) from <http://developer.amazon.com/en-US/blogs/alexa/alexa-skills-kit/2021/03/aiva-health-voice-powered-care-assistant> entire document.
Mavropoulos et al. “A context-aware conversational agent in the rehabilitation domain.” Future Internet 11.11 (2019): 231.Nov. 1, 2019 (Nov. 1, 2019) Retrieved on Oct. 6, 2022 (Oct. 6, 2022) from <https://www.mdpi.com/1999-5903/11/11/231> entire document.
Fadhil. “Beyond patient monitoring: Conversational agents role in telemedicine & healthcare support for home-living elderly individuals.” arXiv preprint arXiv: 1803.06000 (Mar. 3, 2018). <http://arxiv.org/abs/1803.06000> entire document.
International Search Report and Written Opinion in the related Application Serial No. PCT/US2022/038579 on Oct. 28, 2022.
Atasoy et al. “Real-Time motorized electrical hospital bed control with eye-gaze tracking.” Nesrin Aydin Atasoy et al. In Turkish Journal of Electrical Engineering and Computer Sciences. vol. 24, No. 6. Article 46. Received: Mar. 17, 2015; Published Nov. 3, 2015; Final Version: Dec. 6, 2016. https://journals. tubitak.gov.tr/elektrik.
International Search Report and Written Opinion in the related Application Serial No. PCT/US2022/038571 on Nov. 30, 2022.
Reidel et al. “Pilot study of an interactive voice response system to improve medication refill compliance.” BMC medical informatics and decision making 8.1 (2008): 1-8.Oct. 9, 2008 (Oct. 9, 2008) Retrieved on Nov. 5, 2022 (Nov. 5, 2022) from <https://bmcmedinformdecismak.biomedcentral.com/articles/10.1186/1472-6947-8-46> entire document.
Pradhan et al. “Accessibility Came by Accident: Use of Voice-Controlled Intelligent Personal Assistants by People with Disabilities.” Proceedings of the 2018 CHI Conference on human factors in computing systems. 2018. Apr. 26, 2018 (Apr. 26, 2018) Retrieved on Nov. 5, 2022 (Nov. 5, 2022) from <https://dl.acm.org/doi/abs/10.1145/3173574.3174033> entire document.
International Search Report and Written Opinion in the related Application Serial No. PCT/US2022/038550 on Oct. 13, 2022.
International Search Report and Written Opinion in the related Application Serial No. PCT/US2022/038575 on Nov. 7, 2022.
International Search Report and Written Opinion issued in related Application Serial No. PCT/US2022/038554 on Issue date; Oct. 11, 2022.
International Search Report and Written Opinion issued in related Application Serial No. PCT/US2022/038558 on Issue Date; Dec. 8, 2022.
International Search Report and Written Opinion issued in related Application Serial No. PCT/US2022/038573 on Issue date; Oct. 25, 2022.
Tian et al. “Smart healthcare: making medical care more intelligent.” Global Health Journal 3.3 (2019): 62-65.Oct. 14, 2019.
International Search Report and Written Opinion issued in related Application PCT/US2022/038545 on Oct. 18, 2022.
K. Denecke, S. Vaaheesan and A. Arulnathan, “A Mental Health Chatbot for Regulating Emotions (SERMO)—Concept and Usability Test,” in IEEE Transactions on Emerging Topics in Computing, vol. 9, No. 3, pp. 1170-1182, Jul. 1-Sep. 2021, doi: 10.1109/TETC.2020.2974478. (Year: 2021).
Lee, Brian, How Aiva Health Is Creating New Opportunities for COVID-Safe Care, Mar. 4, 2021, Amazon, https://developer.amazon.com/en-US/blogs/alexa/alexa-skills-kit/2021/03/aiva-health-voice-powered-care-assistant (Year: 2021).
Non-Final Office Action issued in related U.S. Appl. No. 17/874,607 on issue Date; Apr. 5, 2024.
Non-Final Office Action issued in related U.S. Appl. No. 17/874,646 on Jun. 20, 2024.
Non-Final Office Action issued in related U.S. Appl. No. 17/874,664 on issue DATE; May 7, 2024.
Non-Final Office Action issued in related U.S. Appl. No. 17/874,693 on May 24, 2024.
Non-Final Office Action issued in related U.S. Appl. No. 17/874,707 on Jun. 6, 2024.
Non-Final Office Action issued in related U.S. Appl. No. 17/874,619 on issue Date; Mar. 6, 2024.
Non-Final Office Action issued in related U.S. Appl. No. 17/874,577 on Aug. 1, 2024.
Final Office Action issued in related U.S. Appl. No. 17/874,619 on Nov. 6, 2024.
Final Office Action issued in related U.S. Appl. No. 17/874,607 on Jan. 10, 2025.
Final Office Action issued in related U.S. Appl. No. 17/874,646 on Feb. 28, 2025.
Final Office Action issued in related U.S. Appl. No. 17/874,664 on Jan. 28, 2025.
Final Office Action issued in related U.S. Appl. No. 17/874,693 on Feb. 20, 2025.
Final Office Action issued in related U.S. Appl. No. 17/874,707 on Feb. 3, 2025
Non-Final Office Action issued in related U.S. Appl. No. 17/874,619 on Mar. 18, 2025.
Notice of Allowance issued in related U.S. Appl. No. 17/874,577 on Mar. 12, 2025.
Non-Final Office Action issued in related U.S. Appl. No. 17/874,607 on May 16, 2025.
Non-Final Office Action issued in related U.S. Appl. No. 17/874,693 on Jun. 17, 2025.
Non-Final Office Action issued in related U.S. Appl. No. 17/874,707 on Jun. 25, 2025.
Notice of Allowance issued in related U.S. Appl. No. 17/874,577 on Apr. 24, 2025.
Notice of Allowance issued in the related U.S. Appl. No. 17/874,577 on Jun. 10, 2025.
Schwartz, “Orbita acquires voice app connecting hospital patients to nurses”, Nov. 19, 2019. (Year: 2019).
X. Ren, G. Spina, S. De Vries, A. Bijkerk, B. Faber and A. Geraedts, “Understanding Physician’s Experience With Conversational Interfaces During Occupational Health Consultation,” in IEEE Access, vol. 8, pp. 119158-119169, 2020, doi: 10.1109/ACCESS.2020.3005733 (Year: 2020).
Final Office Action issued in related U.S. Appl. No. 17/874,607 on Sep. 5, 2025.

(56) References Cited

OTHER PUBLICATIONS

Final Office Action issued in related U.S. Appl. No. 17/874,619 on Oct. 15, 2025.
Final Office Action issued in related U.S. Appl. No. 17/874,693 on Feb. 24, 2026.
Kesari, Ganes, "AI Can Now Detect Depression From Your Voice, And It's Twice As Accurate As Human Practitioners", May 24, 2021, published on www.forbes.com (Year: 2021).
Notice of Allowance issued in related U.S. Appl. No. 17/874,707 on Jan. 23, 2026.
Non-Final Office Action issued in related U.S. Appl. No. 17/874,619 on Mar. 26, 2026.
Non-Final Office Action issued in related U.S. Appl. No. 17/874,607 on Mar. 24, 2026.
Non Final Office Action issued in the related U.S. Appl. No. 17/874,693 on Jul. 1, 2026.
Notice of Allowance issued in related U.S. Appl. No. 17/874,707 on Apr. 23, 2026.

* cited by examiner monitoring the diction of a prescription recipient using a virtual assistant (600)

Figure 7:
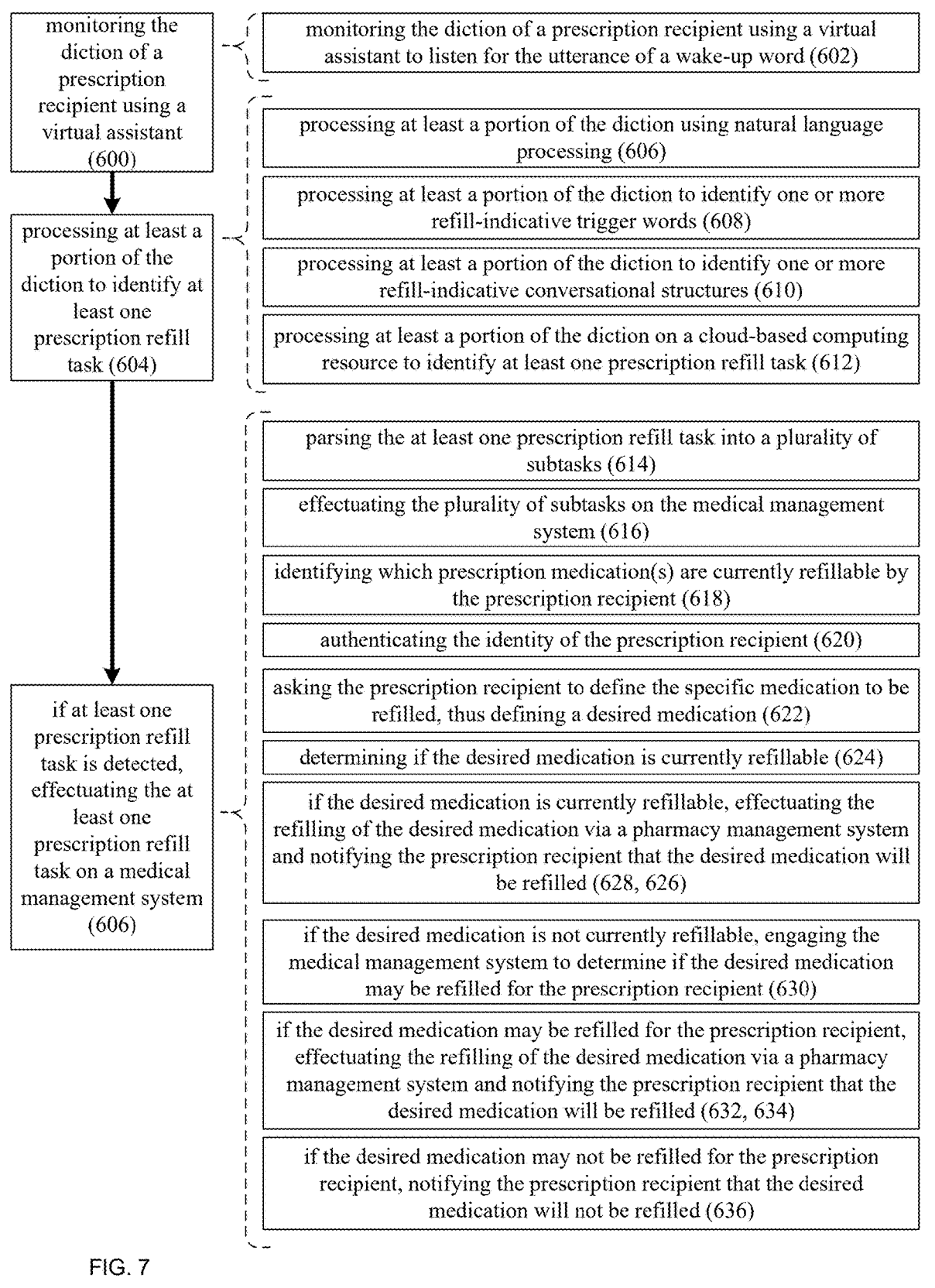

monitoring the diction of a prescription recipient using a virtual assistant to listen for the utterance of a wake-up word (602)

processing at least a portion of the diction to identify at least one prescription refill task (604)

processing at least a portion of the diction using natural language processing (606)

processing at least a portion of the diction to identify one or more refill-indicative trigger words (608)

processing at least a portion of the diction to identify one or more refill-indicative conversational structures (610)

processing at least a portion of the diction on a cloud-based computing resource to identify at least one prescription refill task (612)

if at least one prescription refill task is detected, effectuating the at least one prescription refill task on a medical management system (606)

parsing the at least one prescription refill task into a plurality of subtasks (614)

effectuating the plurality of subtasks on the medical management system (616)

identifying which prescription medication(s) are currently refillable by the prescription recipient (618)

authenticating the identity of the prescription recipient (620)

asking the prescription recipient to define the specific medication to be refilled, thus defining a desired medication (622)

determining if the desired medication is currently refillable (624)

if the desired medication is currently refillable, effectuating the refilling of the desired medication via a pharmacy management system and notifying the prescription recipient that the desired medication will be refilled (628, 626)

if the desired medication is not currently refillable, engaging the medical management system to determine if the desired medication may be refilled for the prescription recipient (630)

if the desired medication may be refilled for the prescription recipient, effectuating the refilling of the desired medication via a pharmacy management system and notifying the prescription recipient that the desired medication will be refilled (632, 634)

if the desired medication may not be refilled for the prescription recipient, notifying the prescription recipient that the desired medication will not be refilled (636)

FIG. 7 interfacing a clinical research system with a virtual assistant accessible by a clinical trial participant (700)

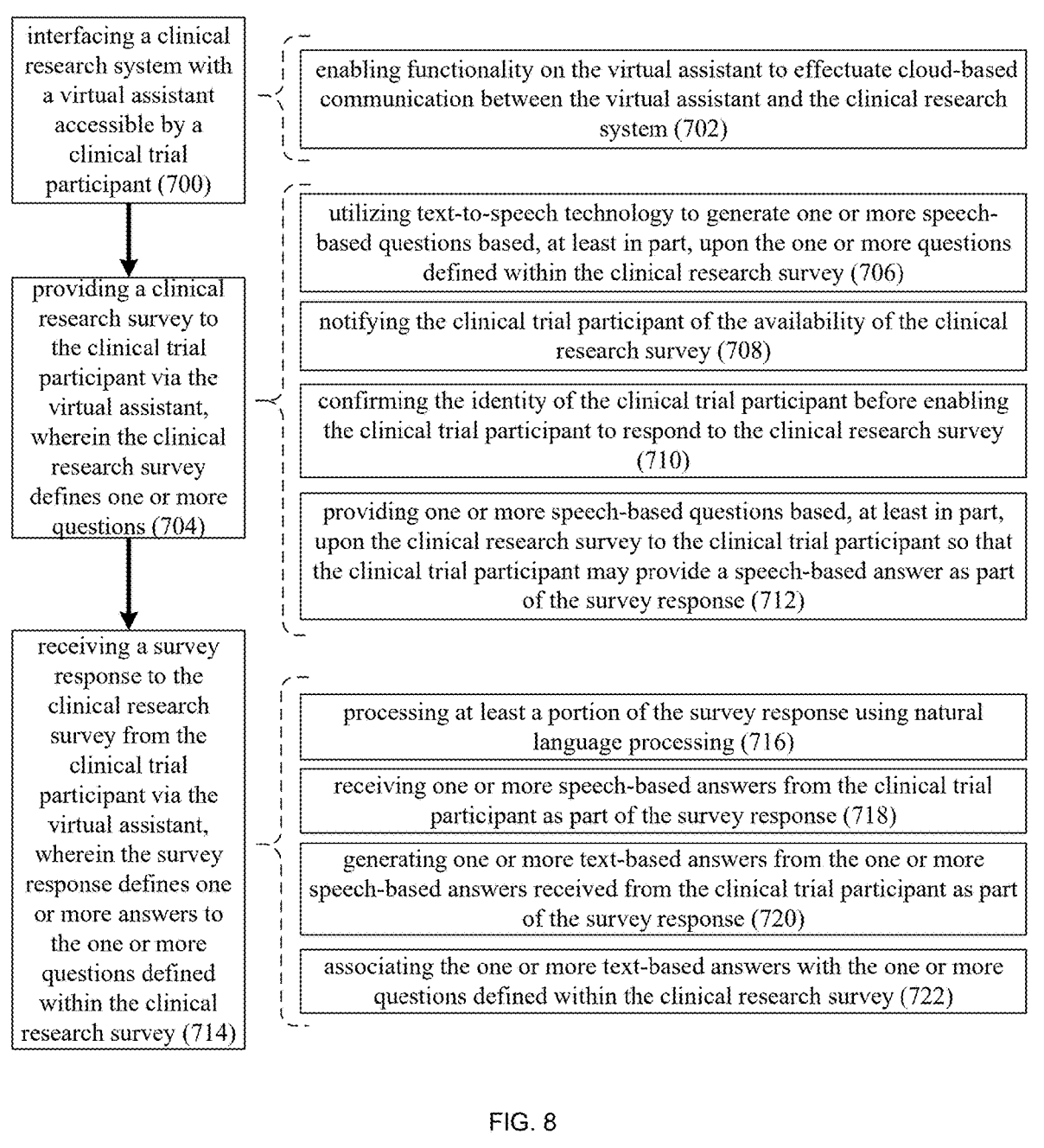

enabling functionality on the virtual assistant to effectuate cloud-based communication between the virtual assistant and the clinical research system (702)

providing a clinical research survey to the clinical trial participant via the virtual assistant, wherein the clinical research survey defines one or more questions (704)

utilizing text-to-speech technology to generate one or more speech-based questions based, at least in part, upon the one or more questions defined within the clinical research survey (706)

notifying the clinical trial participant of the availability of the clinical research survey (708)

confirming the identity of the clinical trial participant before enabling the clinical trial participant to respond to the clinical research survey (710)

providing one or more speech-based questions based, at least in part, upon the clinical research survey to the clinical trial participant so that the clinical trial participant may provide a speech-based answer as part of the survey response (712)

receiving a survey response to the clinical research survey from the clinical trial participant via the virtual assistant, wherein the survey response defines one or more answers to the one or more questions defined within the clinical research survey (714)

processing at least a portion of the survey response using natural language processing (716)

receiving one or more speech-based answers from the clinical trial participant as part of the survey response (718)

generating one or more text-based answers from the one or more speech-based answers received from the clinical trial participant as part of the survey response (720)

associating the one or more text-based answers with the one or more questions defined within the clinical research survey (722)

FIG. 8

HANDSFREE COMMUNICATION SYSTEM AND METHOD

RELATED APPLICATION(S)

This application claims the benefit of U.S. Provisional Application No. 63/226,708, filed on 28 Jul. 2021, the entire contents of which are incorporated herein by reference.

TECHNICAL FIELD

This disclosure relates to communication systems and, more particularly, to communication systems that utilize virtual assistants within the business space.

BACKGROUND

Handsfree communication is becoming very popular. Our cars allow us to verbally communicate with them and virtual assistants (e.g., Apple's Ski and Amazon's Alexa) allow us to obtain information in response to spoken requests, as well as adjust thermostats, dim room lighting, change our television channels, etc.

Unfortunately, the manner in which voice control and virtual assistants have been integrated into business application platforms is often superficial at best. For example, such business application platforms often only allow for voice control of simple cursory tasks . . . as opposed to more complex multi-step processes.

SUMMARY OF DISCLOSURE

Hands Free, Voice-based Control of a Hospital Bed

In one implementation, a computer-implemented method is executed on a computing device and includes: monitoring the diction of a patient within a hospital room; processing at least a portion of the diction to identify at least one bed-control-command to be performed on a hospital bed within the hospital room; and if at least one bed-control-command is detected, effectuating the at least one bed-control-command on the hospital bed within the hospital room.

One or more of the following features may be included. Monitoring the diction of a patient within a hospital room may include: monitoring the diction of a patient within a hospital room using a virtual assistant. The virtual assistant may be interfaced with the hospital bed within the hospital room. Interfacing the virtual assistant with the hospital bed within the hospital room may include: enabling functionality on the virtual assistant to effectuate cloud-based communication between the virtual assistant and the hospital bed within the hospital room. Monitoring the diction of a patient within a hospital room may include: monitoring the diction of a patient within a hospital room to listen for the utterance of a wake-up word. Processing at least a portion of the diction to identify at least one bed-control-command to be performed on a hospital bed within the hospital room may include: processing at least a portion of the diction on a cloud-based computing resource to identify at least one bed-control-command to be performed on a hospital bed within the hospital room. The at least one bed-control-command to be performed on a hospital bed within the hospital room may include one or more of: a head raise/lower bed-control-command; a knee raise/lower bed-control-command; a feet raise/lower bed-control-command; a bed raise/lower bed-control-command; a heater on/off bed-control-command; and a massager on/off bed-control-command. At least a portion of the diction may be processed to identify at least one supplemental command to be performed within the hospital room. Processing at least a portion of the diction to identify at least one supplemental command to be performed within the hospital room may include: processing at least a portion of the diction on a cloud-based computing resource to identify at least one supplemental command to be performed within the hospital room. The at least one supplemental command to be performed within the hospital room may include one or more of: placing a food/beverage order; requesting medication; contacting the nurse's station; calling for emergency assistance; controlling a room lighting system; and controlling a television.

In another implementation, a computer program product resides on a computer readable medium and has a plurality of instructions stored on it. When executed by a processor, the instructions cause the processor to perform operations including monitoring the diction of a patient within a hospital room; processing at least a portion of the diction to identify at least one bed-control-command to be performed on a hospital bed within the hospital room; and if at least one bed-control-command is detected, effectuating the at least one bed-control-command on the hospital bed within the hospital room.

One or more of the following features may be included. Monitoring the diction of a patient within a hospital room may include: monitoring the diction of a patient within a hospital room using a virtual assistant. The virtual assistant may be interfaced with the hospital bed within the hospital room. Interfacing the virtual assistant with the hospital bed within the hospital room may include: enabling functionality on the virtual assistant to effectuate cloud-based communication between the virtual assistant and the hospital bed within the hospital room. Monitoring the diction of a patient within a hospital room may include: monitoring the diction of a patient within a hospital room to listen for the utterance of a wake-up word. Processing at least a portion of the diction to identify at least one bed-control-command to be performed on a hospital bed within the hospital room may include: processing at least a portion of the diction on a cloud-based computing resource to identify at least one bed-control-command to be performed on a hospital bed within the hospital room. The at least one bed-control-command to be performed on a hospital bed within the hospital room may include one or more of: a head raise/lower bed-control-command; a knee raise/lower bed-control-command; a feet raise/lower bed-control-command; a bed raise/lower bed-control-command; a heater on/off bed-control-command; and a massager on/off bed-control-command. At least a portion of the diction may be processed to identify at least one supplemental command to be performed within the hospital room. Processing at least a portion of the diction to identify at least one supplemental command to be performed within the hospital room may include: processing at least a portion of the diction on a cloud-based computing resource to identify at least one supplemental command to be performed within the hospital room. The at least one supplemental command to be performed within the hospital room may include one or more of: placing a food/beverage order; requesting medication; contacting the nurse's station; calling for emergency assistance; controlling a room lighting system; and controlling a television.

In another implementation, a computing system includes a processor and a memory system configured to perform operations including monitoring the diction of a patient within a hospital room; processing at least a portion of the diction to identify at least one bed-control-command to be performed on a hospital bed within the hospital room; and if at least one bed-control-command is detected, effectuating the at least one bed-control-command on the hospital bed within the hospital room.

One or more of the following features may be included. Monitoring the diction of a patient within a hospital room may include: monitoring the diction of a patient within a hospital room using a virtual assistant. The virtual assistant may be interfaced with the hospital bed within the hospital room. Interfacing the virtual assistant with the hospital bed within the hospital room may include: enabling functionality on the virtual assistant to effectuate cloud-based communication between the virtual assistant and the hospital bed within the hospital room. Monitoring the diction of a patient within a hospital room may include: monitoring the diction of a patient within a hospital room to listen for the utterance of a wake-up word. Processing at least a portion of the diction to identify at least one bed-control-command to be performed on a hospital bed within the hospital room may include: processing at least a portion of the diction on a cloud-based computing resource to identify at least one bed-control-command to be performed on a hospital bed within the hospital room. The at least one bed-control-command to be performed on a hospital bed within the hospital room may include one or more of: a head raise/lower bed-control-command; a knee raise/lower bed-control-command; a feet raise/lower bed-control-command; a bed raise/lower bed-control-command; a heater on/off bed-control-command; and a massager on/off bed-control-command. At least a portion of the diction may be processed to identify at least one supplemental command to be performed within the hospital room. Processing at least a portion of the diction to identify at least one supplemental command to be performed within the hospital room may include: processing at least a portion of the diction on a cloud-based computing resource to identify at least one supplemental command to be performed within the hospital room. The at least one supplemental command to be performed within the hospital room may include one or more of: placing a food/beverage order; requesting medication; contacting the nurse's station; calling for emergency assistance; controlling a room lighting system; and controlling a television.

The details of one or more implementations are set forth in the accompanying drawings and the description below. Other features and advantages will become apparent from the description, the drawings, and the claims.

BRIEF DESCRIPTION OF THE DRAWINGS

FIG. 7 is a flowchart of the communication process of FIG. 1 according to another embodiment of the present disclosure;

FIG. 8 is a flowchart of the communication process of FIG. 1 according to another embodiment of the present disclosure;

Like reference symbols in the various drawings indicate like elements.

DETAILED DESCRIPTION OF THE PREFERRED EMBODIMENTS

System Overview

Figure 1:
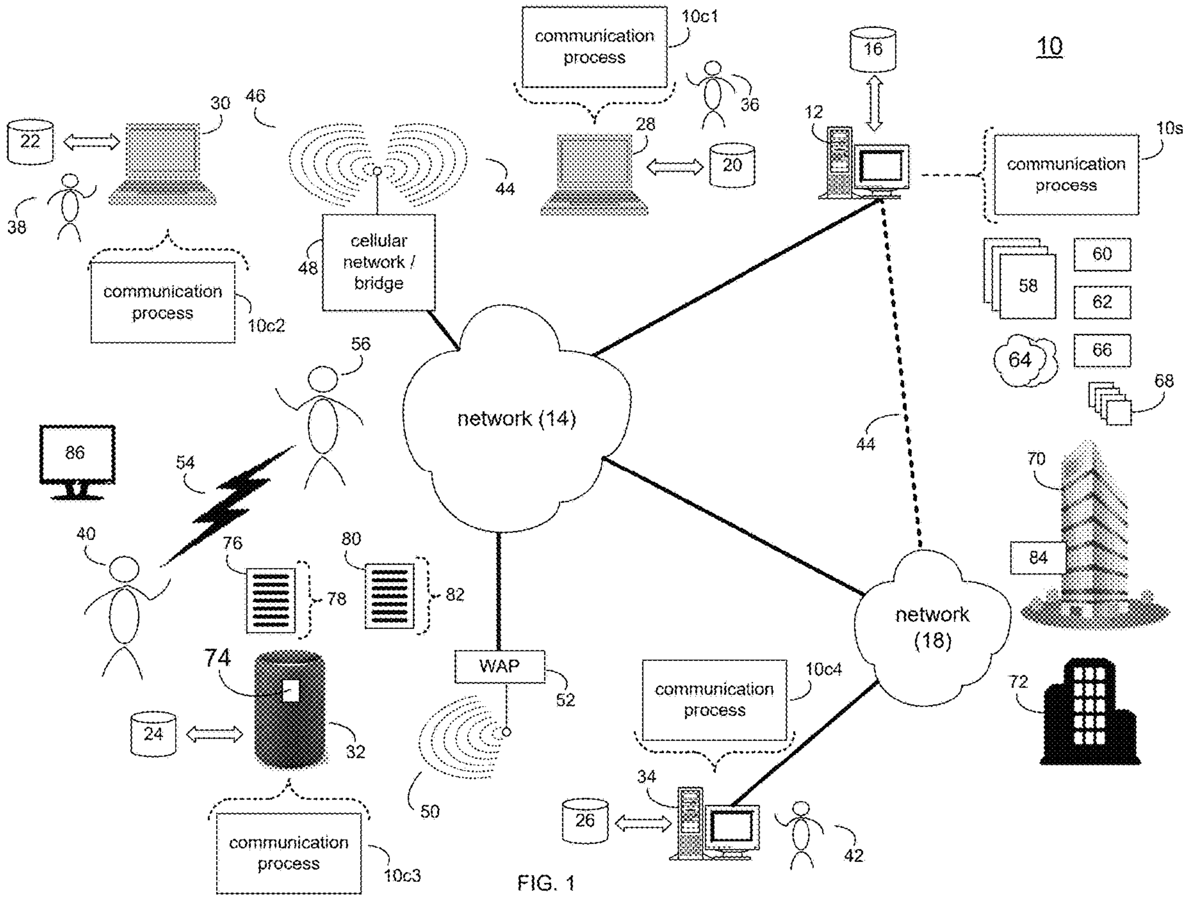
FIG. 1 is a diagrammatic view of a distributed computing network including a computing device that executes a communication process according to an embodiment of the present disclosure.

Referring to FIG. 1, there is shown communication process 10. Communication process 10 may be implemented as a server-side process, a client-side process, or a hybrid server-side/client-side process. For example, communication process 10 may be implemented as a purely server-side process via communication process 10*s*. Alternatively, communication process 10 may be implemented as a purely client-side process via one or more of communication process 10*c*1, communication process 10*c*2, communication process 10*c*3, and communication process 10*c*4. Alternatively still, communication process 10 may be implemented as a hybrid server-side/client-side process via communication process 10*s* in combination with one or more of communication process 10*c*1, communication process 10*c*2, communication process 10*c*3, and communication process 10*c*4. Accordingly, communication process 10 as used in this disclosure may include any combination of communication process 10*s*, communication process 10*c*1, communication process 10*c*2, communication process 10*c*3, and communication process 10*c*4.

Communication process 10*s* may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, or a cloud-based computing platform.

The instruction sets and subroutines of communication process 10*s*, which may be stored on storage device 16 coupled to computing device 12, may be executed by one or more processors (not shown) and one or more memory architectures (not shown) included within computing device 12. Examples of storage device 16 may include but are not limited to: a hard disk drive; a redundant array of independent disks (RAID) device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of communication processes 10*c*1, 10*c*2, 10*c*3, 10*c*4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX platform). The instruction sets and subroutines of communication processes 10$c$1, 10$c$2, 10$c$3, 10$c$4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to, a smartphone (not shown), a personal digital assistant (not shown), a tablet computer (not shown), laptop computers 28, 30, virtual assistant 32, personal computer 34, a notebook computer (not shown), a server computer (not shown), a gaming console (not shown), and a dedicated network device (not shown). Client electronic devices 28, 30, 32, 34 may each execute an operating system, examples of which may include but are not limited to Microsoft Windows™, Android™, iOS™, Linux™, or a custom operating system.

Users 36, 38, 40, 42 may access communication process 10 directly through network 14 or through secondary network 18. Further, communication process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, laptop computer 28 and laptop computer 30 are shown wirelessly coupled to network 14 via wireless communication channels 44, 46 (respectively) established between laptop computers 28, 30 (respectively) and cellular network/bridge 48, which is shown directly coupled to network 14. Further, virtual assistant 32 is shown wirelessly coupled to network 14 via wireless communication channel 50 established between virtual assistant 32 and wireless access point (i.e., WAP 52), which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between laptop computer 32 and WAP 52. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

Communication Process Overview

As will be discussed below in greater detail, communication process 10 may be configured to monitor the conversations between various entities (e.g., users, professionals, callers, patients) so that e.g., professionals may be monitored and assistance may be rendered.

Automated Monitoring for Bias Detection

Figure 2:
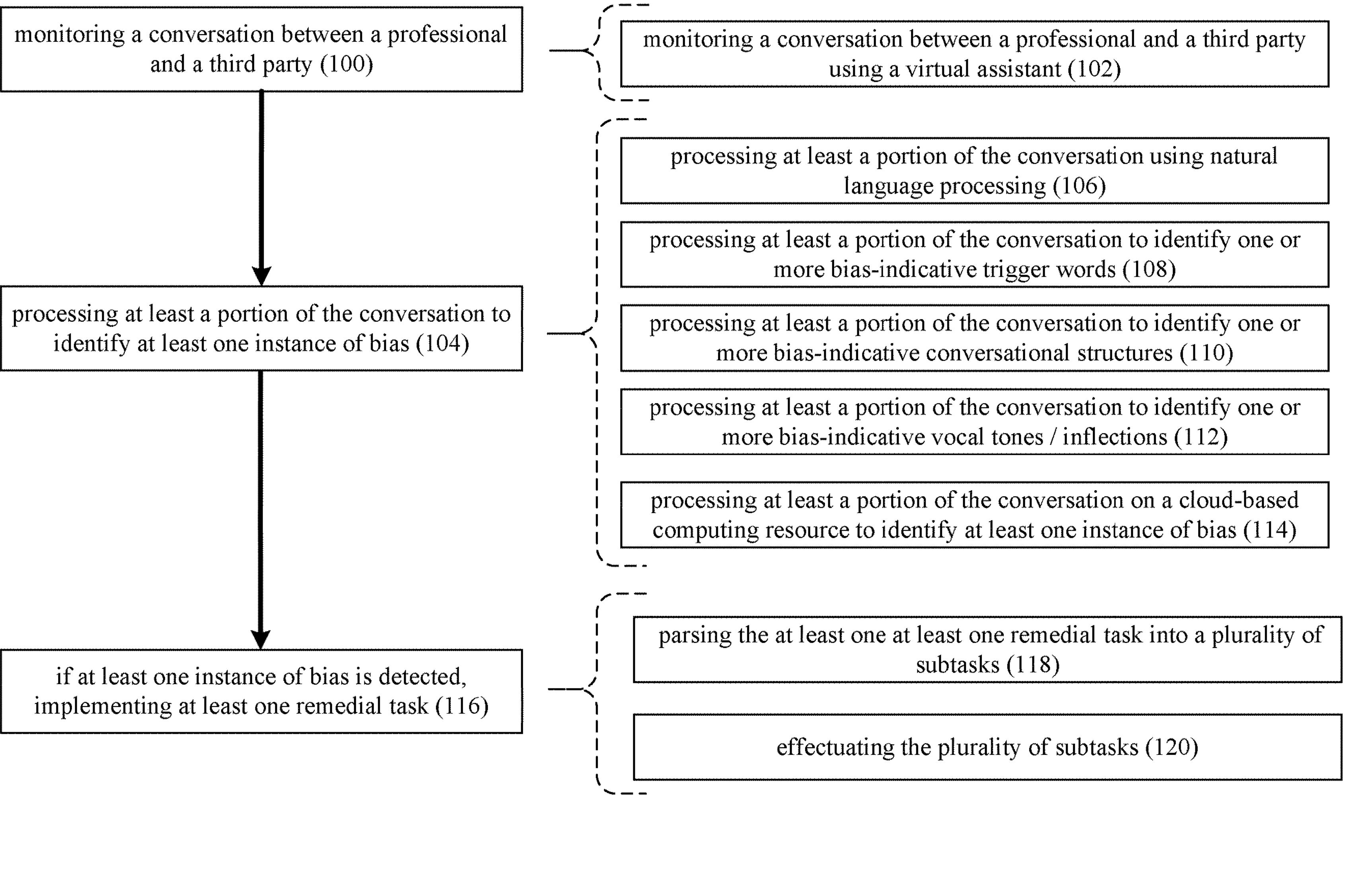
FIG. 2 is a flowchart of the communication process of FIG. 1 according to an embodiment of the present disclosure.

Referring also to FIG. 2, communication process 10 may monitor 100 a conversation (e.g., conversation 54) between a professional (e.g., user 40) and a third party (e.g., third party 56).

The conversation (e.g., conversation 54) between a professional (e.g., user 40) and a third party (e.g., third party 56) may include one or more of: an in-person conversation (e.g., conversation 54) between a professional (e.g., user 40) and a third party (e.g., third party 56); a telephone conversation (e.g., conversation 54) between a professional (e.g., user 40) and a third party (e.g., third party 56); and an audio visual (AV) conversation (e.g., conversation 54) between a professional (e.g., user 40) and a third party (e.g., third party 56).

- In-Person Conversation: Examples of such an in-person conversation (e.g., conversation 54) may include but are not limited to an in-person conversation (e.g., conversation 54) between a medical professional (e.g., user 40) and a patient (e.g., third party 56); an in-person conversation (e.g., conversation 54) between a supervisor (e.g., user 40) and an employee (e.g., third party 56); and an in-person conversation (e.g., conversation 54) between a help center employee (e.g., user 40) and a caller (e.g., third party 56).
- Telephone Conversation: Examples of such a telephone conversation (e.g., conversation 54) may include but are not limited to a telephone conversation (e.g., conversation 54) between a medical professional (e.g., user 40) and a patient (e.g., third party 56); a telephone conversation (e.g., conversation 54) between a supervisor (e.g., user 40) and an employee (e.g., third party 56); and a telephone conversation (e.g., conversation 54) between a help center employee (e.g., user 40) and a caller (e.g., third party 56).
- AV Conversation: Examples of such an AV conversation (e.g., conversation 54) may include but are not limited to an AV conversation (e.g., conversation 54) between a medical professional (e.g., user 40) and a patient (e.g., third party 56); an AV conversation (e.g., conversation 54) between a supervisor (e.g., user 40) and an employee (e.g., third party 56); and an AV conversation (e.g., conversation 54) between a help center employee (e.g., user 40) and a caller (e.g., third party 56).

When monitoring 100 a conversation (e.g., conversation 54) between a professional (e.g., user 40) and a third party (e.g., third party 56), communication process 10 may monitor 102 a conversation (e.g., conversation 54) between a professional (e.g., user 40) and a third party (e.g., third party 56) using a virtual assistant (e.g., virtual assistant 32). Additionally/alternatively and when monitoring 100 a conversation (e.g., conversation 54) between a professional (e.g., user 40) and a third party (e.g., third party 56), communication process 10 may directly monitor the telephone conversation (e.g., conversation 54) between the professional (e.g., user 40) and the third party (e.g., third party 56) and/or directly monitor the AV conversation (e.g., conversation 54) between the professional (e.g., user 40) and a third party (e.g., third party 56).

As is known in the art, a virtual assistant is a software agent that can perform tasks or services for an individual based on commands or questions. The term "chatbot" is sometimes used to refer to virtual assistants generally or specifically accessed by online chat. In some cases, online chat programs are exclusively for entertainment purposes. Some virtual assistants are able to interpret human speech and respond via synthesized voices. Users can ask their assistants questions, control home automation devices and media playback via voice, and manage other basic tasks such as email, to-do lists, and calendars with speech-based commands. A similar concept, however with differences, lays under the dialogue systems. As of 2017, the capabilities and usage of virtual assistants are expanding rapidly, with new products entering the market and a strong emphasis on both email and voice user interfaces. Apple and Google have large installed bases of users on smartphones. Microsoft has a large installed base of Windows-based personal computers, smartphones and smart speakers. Amazon has a large install base for smart speakers. Conversica has over 100 million engagements via its email and SMS interface intelligent virtual assistants for business.

Communication process 10 may process 104 at least a portion of the conversation (e.g., conversation 54) to identify at least one instance of bias, wherein the at least one instance of bias may include but is not limited to one or more of: at least one instance of racial bias (i.e., treating people differently based upon their race); at least one instance of gender bias (i.e., treating people differently based upon their gender); at least one instance of military status bias (i.e., treating people differently based upon their military status); at least one instance of disability bias (i.e., treating people differently based upon their disabilities); and at least one instance of age bias (i.e., treating people differently based upon their age). This above-described instances of bias are intended to be illustrative and not all inclusive. Accordingly, other instances of bias are possible and are considered to be within the scope of this disclosure.

When processing 104 at least a portion of the conversation (e.g., conversation 54) to identify at least one instance of bias, communication process 10 may process 106 at least a portion of the conversation (e.g., conversation 54) using natural language processing. As is known in the art, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

When processing 104 at least a portion of the conversation (e.g., conversation 54) to identify at least one instance of bias, communication process 10 may also:

- process 108 at least a portion of the conversation (e.g., conversation 54) to identify one or more bias-indicative trigger words (e.g., "honey", "darling", "sweetie", "old", "aged");
- process 110 at least a portion of the conversation (e.g., conversation 54) to identify one or more bias-indicative conversational structures (e.g., "people like you", "where are you from?", "emotional types"); and process 112 at least a portion of the conversation (e.g., conversation 54) to identify one or more bias-indicative vocal tones/inflections (e.g., condescending tones/inflections, sarcastic tones/inflections, derogatory tones/inflections).

The above-described bias-indicative trigger words, bias-indicative conversational structures, and bias-indicative vocal tones/inflections may be manually defined or may be automatically defined. For example, an administrator of communication process 10 may manually define one or more lists (e.g., lists 58) that identify such bias-indicative trigger words, bias-indicative conversational structures, and bias-indicative vocal tones/inflections. Additionally/alternatively, an administrator of communication process 10 may define seed data (e.g., seed data 60) that may be processed via artificial intelligence (AI) process 62 that may be configured to expand seed data 60 to define the above-referenced lists (e.g., lists 58).

As is known in the art, a machine learning system or model may generally include an algorithm or combination of algorithms that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

In order to harness greater processing power, when processing 104 at least a portion of the conversation (e.g., conversation 54) to identify at least one instance of bias, communication process 10 may process 114 at least a portion of the conversation (e.g., conversation 54) on a cloud-based computing resource (e.g., cloud resource 64) to identify at least one instance of bias. As is known in the art, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users.

If at least one instance of bias is detected, communication process 10 may implement 116 at least one remedial task (e.g., task 66), wherein these remedial tasks (e.g., task 66) may include one or more of: notifying management; encouraging supplemental training; requiring supplemental training; and intervening in the conversation (e.g., conversation 54).

- Notifying Management: A supervisor (e.g., user 42) of user 40 (as well as user 40 themselves) may be notified by communication process 10. Accordingly, the at least one instance of bias identified by communication process 10 may be addressed more discretely (by notifying user 40 only) or less discretely (by notifying user 42).
- Encouraging Supplemental Training: In less problematic situations, user 40 may be asked/encouraged to attend some form of supplemental training to address the at least one instance of bias identified by communication process 10.
- Requiring Supplemental Training: In more problematic situations, user 40 may be required to attend some form of supplemental training to address the at least one instance of bias identified by communication process 10.
- Intervening in the Conversation: In highly problematic situations, communication process 10 may intervene in the conversation (e.g., conversation 54) by e.g., looping in management or terminating the conversation (e.g., conversation 54) to effectuate some form of damage control.

As would be expected, when implementing 116 at least one remedial task (e.g., task 66), communication process 10 may parse 118 the at least one at least one remedial task (e.g., task 66) into a plurality of subtasks (e.g., subtasks 68), wherein communication process 10 may then effectuate 120 the plurality of subtasks (e.g., subtasks 68). For example, in order to accomplish task 66, communication process 10 may effectuate a plurality of discrete subtasks (e.g., subtasks 68), examples of which may include but are not limited to contacting the supervisor of user 40 and providing a private guidance message to user 40.

Automated Monitoring for Suicide Prevention/Depression Detection

Figure 3:
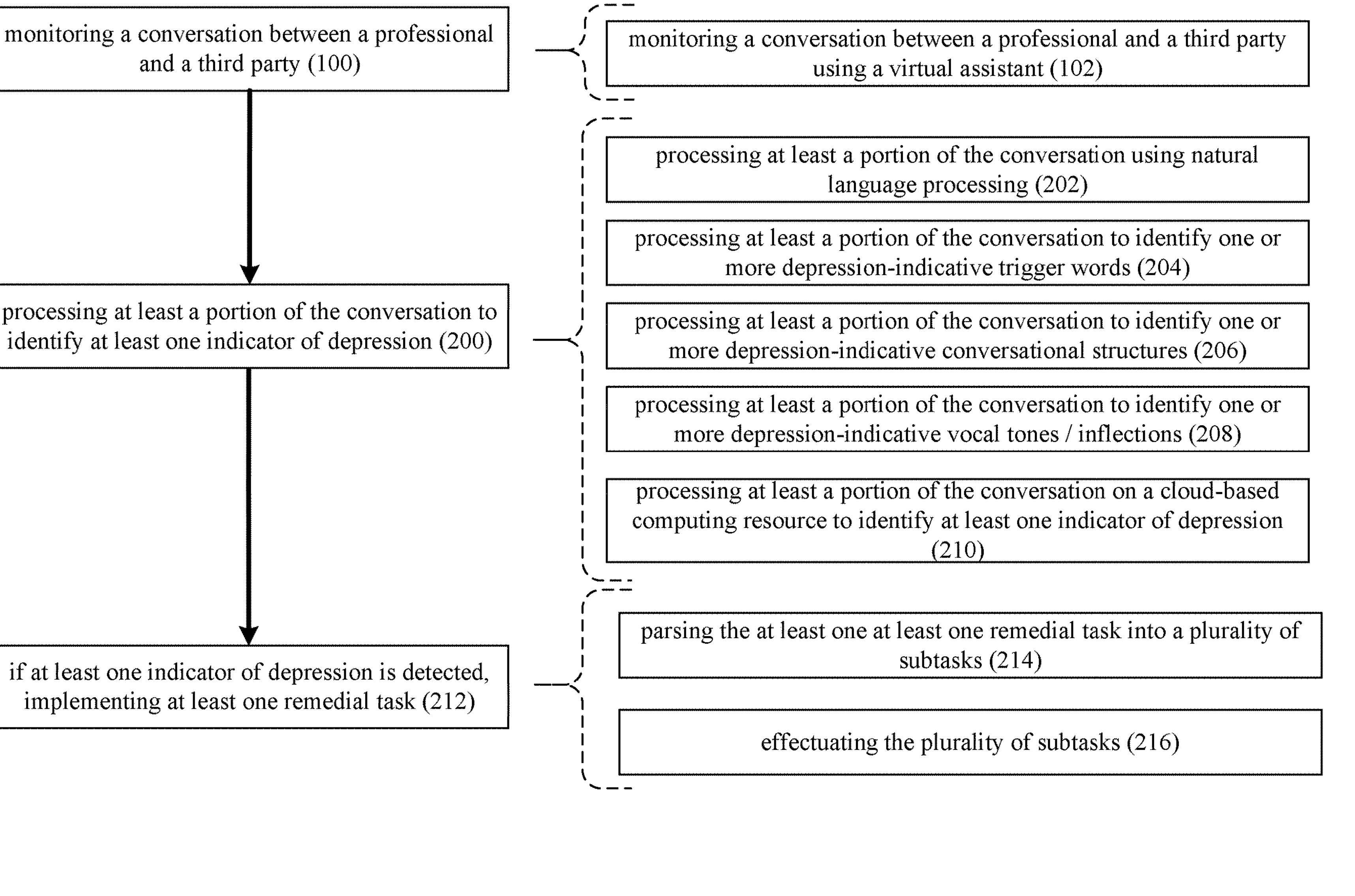
FIG. 3 is a flowchart of the communication process of FIG. 1 according to another embodiment of the present disclosure.

Referring also to FIG. 3 and as discussed above, communication process 10 may monitor 100 a conversation (e.g., conversation 54) between a professional (e.g., user 40) and a third party (e.g., third party 56).

As also discussed above, the conversation (e.g., conversation 54) between a professional (e.g., user 40) and a third party (e.g., third party 56) may include one or more of: an in-person conversation (e.g., conversation 54) between a professional (e.g., user 40) and a third party (e.g., third party 56); a telephone conversation (e.g., conversation 54) between a professional (e.g., user 40) and a third party (e.g., third party 56); and an AV conversation (e.g., conversation 54) between a professional (e.g., user 40) and a third party (e.g., third party 56).

- In-Person Conversation: Examples of such an in-person conversation (e.g., conversation 54) may include but are not limited to an in-person conversation (e.g., conversation 54) between a medical professional (e.g., user 40) and a patient (e.g., third party 56); an in-person conversation (e.g., conversation 54) between a supervisor (e.g., user 40) and an employee (e.g., third party 56); and an in-person conversation (e.g., conversation 54) between a help center employee (e.g., user 40) and a caller (e.g., third party 56).
- Telephone Conversation: Examples of such a telephone conversation (e.g., conversation 54) may include but are not limited to a telephone conversation (e.g., conversation 54) between a medical professional (e.g., user 40) and a patient (e.g., third party 56); a telephone conversation (e.g., conversation 54) between a supervisor (e.g., user 40) and an employee (e.g., third party 56); and a telephone conversation (e.g., conversation 54) between a help center employee (e.g., user 40) and a caller (e.g., third party 56).
- AV Conversation: Examples of such an AV conversation (e.g., conversation 54) may include but are not limited to an AV conversation (e.g., conversation 54) between a medical professional (e.g., user 40) and a patient (e.g., third party 56); an AV conversation (e.g., conversation 54) between a supervisor (e.g., user 40) and an employee (e.g., third party 56); and an AV conversation (e.g., conversation 54) between a help center employee (e.g., user 40) and a caller (e.g., third party 56).

Further and as discussed above, when monitoring 100 a conversation (e.g., conversation 54) between a professional (e.g., user 40) and a third party (e.g., third party 56), communication process 10 may monitor 102 a conversation (e.g., conversation 54) between a professional (e.g., user 40) and a third party (e.g., third party 56) using a virtual assistant (e.g., virtual assistant 32). Additionally/alternatively and when monitoring 100 a conversation (e.g., conversation 54) between a professional (e.g., user 40) and a third party (e.g., third party 56), communication process 10 may directly monitor the telephone conversation (e.g., conversation 54) between the professional (e.g., user 40) and the third party (e.g., third party 56) and/or directly monitor the AV conversation (e.g., conversation 54) between the professional (e.g., user 40) and a third party (e.g., third party 56).

Communication process 10 may process 200 at least a portion of the conversation (e.g., conversation 54) to identify at least one indicator of depression, wherein the at least one indicator of depression may include one or more of: an indicator of negative self-talk (e.g., an indicator that the third party 56 has a low opinion of themself and/or talks about themself in a derogatory fashion); an indicator of a possibility of self-harm (e.g., an indicator that third party 56 may hurt/harm themself); an indicator of a possibility of alcohol abuse (e.g., an indicator that third party 56 may abuse alcohol to cope with their situation); an indicator of a possibility of drug abuse (e.g., an indicator that third party 56 abuse drugs to cope with their situation); and an indicator of a possibility of suicide (e.g., an indicator that third party 56 may attempt to take their own life to cope with their situation). This above-described indicators of depression are intended to be illustrative and not all inclusive. Accordingly, other indicator of depression are possible and are considered to be within the scope of this disclosure When processing 200 at least a portion of the conversation (e.g., conversation 54) to identify at least one indicator of depression, communication process 10 may process 202 at least a portion of the conversation (e.g., conversation 54) using natural language processing. As discussed above, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

When processing 200 at least a portion of the conversation (e.g., conversation 54) to identify at least one indicator of depression, communication process 10 may also:

- process 204 at least a portion of the conversation (e.g., conversation 54) to identify one or more depression-indicative trigger words (e.g., awful, hopeless, suicide, worthless);
- process 206 at least a portion of the conversation (e.g., conversation 54) to identify one or more depression-indicative conversational structures (e.g., "can't take it anymore", "there is nothing left", "why bother", "not worth it"; and/or
- process 208 at least a portion of the conversation (e.g., conversation 54) to identify one or more depression-indicative vocal tones/inflections (e.g., sad tones/inflections, hopeless tones/inflections, derogatory tones/inflections).

The above-described depression-indicative trigger words, depression-indicative conversational structures, and depression-indicative vocal tones/inflections may be manually defined or may be automatically defined. For example, an administrator of communication process 10 may manually define one or more lists (e.g., lists 58) that identify such depression-indicative trigger words, depression-indicative conversational structures, and depression-indicative vocal tones/inflections. Additionally/alternatively, an administrator of communication process 10 may define seed data (e.g., seed data 60) that may be processed via artificial intelligence (AI) process 62 that may be configured to expand seed data 60 to define the above-referenced lists (e.g., lists 58).

In order to harness greater processing power, when processing 200 at least a portion of the conversation (e.g., conversation 54) to identify at least one indicator of depression, communication process 10 may process 210 at least a portion of the conversation (e.g., conversation 54) on a cloud-based computing resource (e.g., cloud resource 64) to identify at least one indicator of depression. As discussed above, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users.

If at least one indicator of depression is detected, communication process 10 may implement 212 at least one remedial task (e.g., task 66), wherein these remedial tasks (e.g., task 66) may include one or more of: notifying management; notifying emergency services; notifying law enforcement; modifying the conversation (e.g., conversation 54); and intervening in the conversation (e.g., conversation 54).

- Notifying Management: In less problematic situations, a supervisor (e.g., user 42) of user 40 (as well as user 40 themselves) may be notified by communication process 10 concerning the indicator of depression detected with respect to third party 56.
- Notifying Emergency Services: In more problematic situations, communication process 10 may notify emergency services to address the indicator of depression detected with respect to third party 56.
- Notifying Law Enforcement: In more problematic situations, communication process 10 may notify law enforcement to address the indicator of depression detected with respect to third party 56.
- Modifying the Conversation: In more problematic situations, communication process 10 may modify the conversation (e.g., by providing guidance to user 40) to steer the conversation into a desired area.
- Intervening in the Conversation: In highly problematic situations, communication process 10 may intervene in the conversation (e.g., conversation 54) by e.g., looping in management to triage and/or gain control of the situation (as well as notifying emergency services/law enforcement).

As discussed above, when implementing 212 at least one remedial task (e.g., task 66), communication process 10 may parse 214 the at least one at least one remedial task (e.g., task 66) into a plurality of subtasks (e.g., subtasks 68), wherein communication process 10 may then effectuate 216 the plurality of subtasks (e.g., subtasks 68). For example, in order to accomplish task 66, communication process 10 may effectuate a plurality of discrete subtasks (e.g., subtasks 68), examples of which may include but are not limited to contacting the supervisor of user 40 and providing a private guidance message to user 40.

Figure 4:
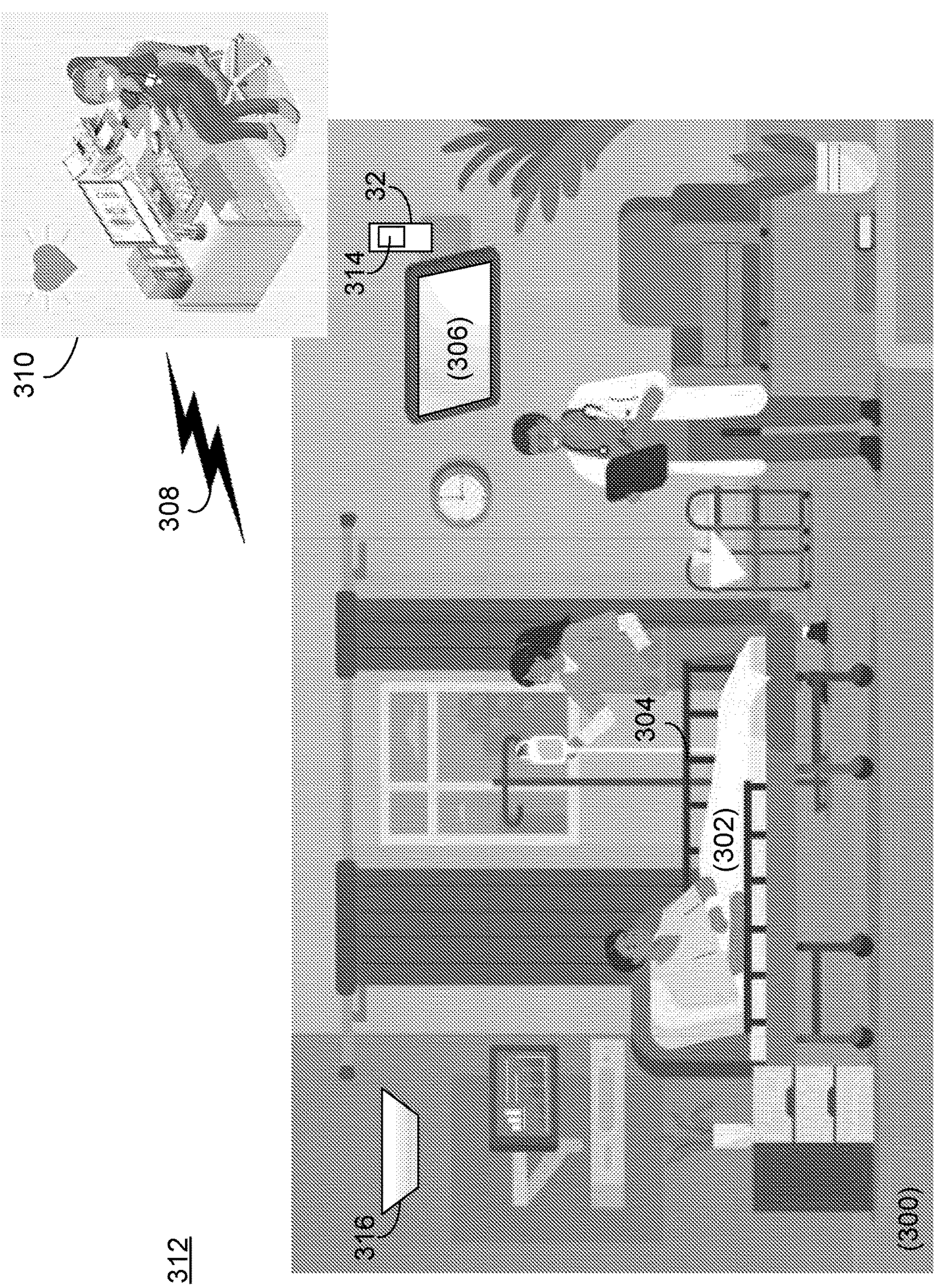
FIG. 4 is a diagrammatic view of a hospital room (including a hospital bed and a television) according to an embodiment of the present disclosure.

Referring also to FIG. 4 and as will be discussed below in greater detail, communication process 10 may be configured to provide a new level of convenience and connectivity for patients when admitted to a hospital. Specifically, hospital rooms (e.g., hospital room 300) typically include a corded controller (not shown) that enables a patient (e.g., patient 302) within the hospital to e.g., contact the nurse's station, and control the hospital bed (e.g., hospital bed 304) and the television (e.g., television 306). Unfortunately, this corded controller (not shown) is often difficult to locate and unsanitary to touch.

Hands Free, Voice-Based Interaction with Medical Staff in a Hospital

Figure 5:
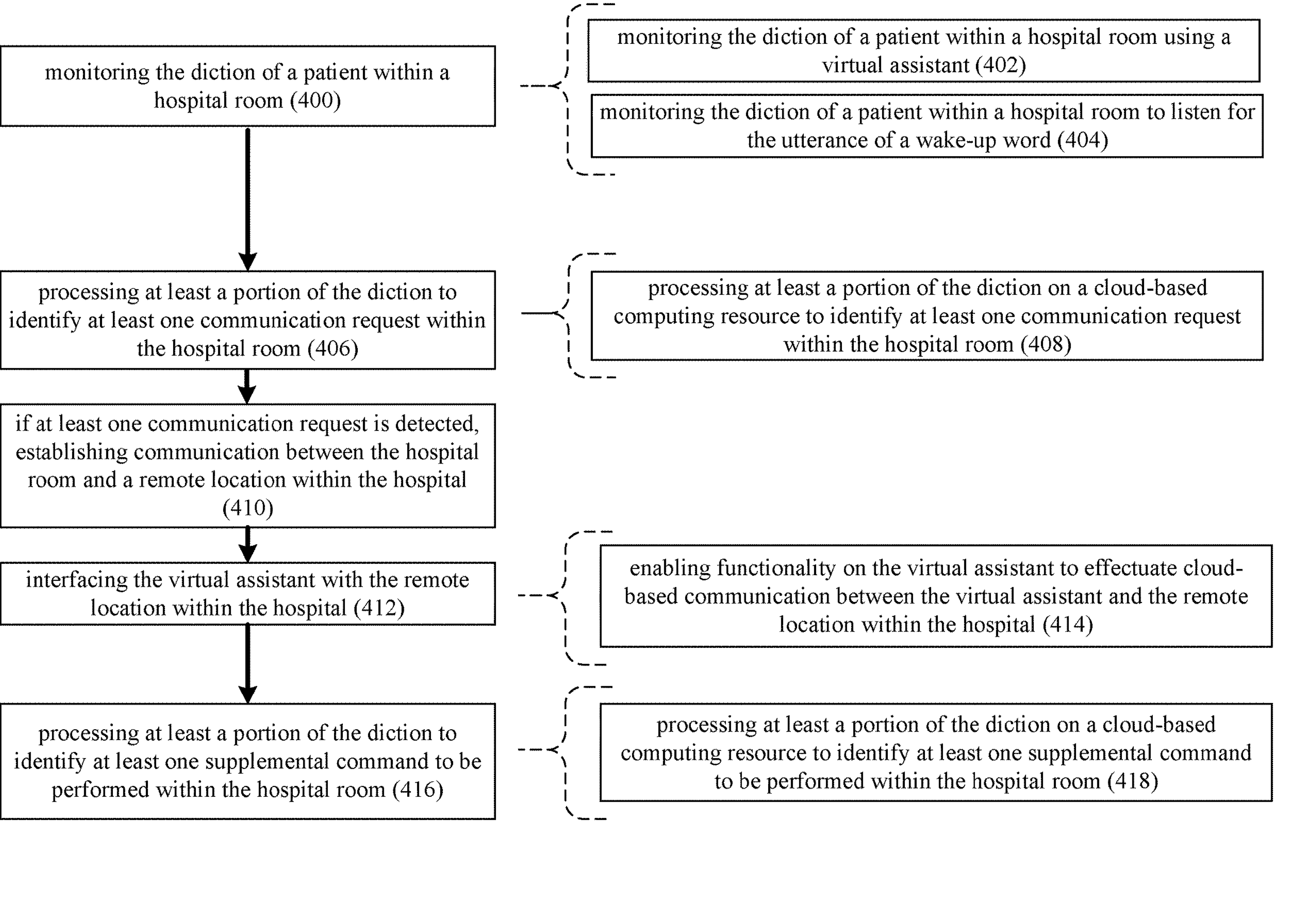
FIG. 5 is a flowchart of the communication process of FIG. 1 according to another embodiment of the present disclosure.

Referring also to FIG. 5, communication process 10 may monitor 400 the diction of a patient (e.g., patient 302) within a hospital room (e.g., hospital room 300). When monitoring 400 the diction of a patient (e.g., patient 302) within a hospital room (e.g., hospital room 300), communication process 10 may monitor 402 the diction of a patient (e.g., patient 302) within a hospital room (e.g., hospital room 300) using a virtual assistant (e.g., virtual assistant 32).

Additionally and when monitoring 400 the diction of a patient (e.g., patient 302) within a hospital room (e.g., hospital room 300), communication process 10 may monitor 404 the diction of a patient (e.g., patient 302) within a hospital room (e.g., hospital room 300) to listen for the utterance of a wake-up word. Examples of such wake-up words may include but are not limited to "Siri", "Alexa", "Google" and "Edera".

Communication process 10 may process 406 at least a portion of the diction to identify at least one communication request within the hospital room (e.g., hospital room 300), wherein examples of such communication requests within the hospital room (e.g., hospital room 300) may include but are not limited to one or more of: placing a food/beverage order; requesting medication; contacting the nurse's station; and calling for emergency assistance.

- Placing a Food/Beverage Order; For example, patient (e.g., patient 302) may order lunch by saying "Hey Edera, I would like to order lunch".
- Requesting Medication; For example, patient (e.g., patient 302) may request medication by saying "Hey Edera, can I please have my pain medication".
- Contacting the Nurse's Station; For example, patient (e.g., patient 302) may request non-emergency assistance by saying "Hey Edera, can I please have some assistance getting to the bathroom".
- Calling for Emergency Assistance: For example, patient (e.g., patient 302) may request emergency assistance by saying "Hey Edera, Help! I am having chest pains".

When processing 406 at least a portion of the diction to identify at least one communication request (e.g., placing a food/beverage order; requesting medication; contacting the nurse's station; and calling for emergency assistance) within the hospital room (e.g., hospital room 300), communication process 10 may process at least a portion of the diction using natural language processing. As discussed above, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

In order to harness greater processing power, when processing 406 at least a portion of the diction to identify at least one communication request (e.g., placing a food/beverage order; requesting medication; contacting the nurse's station; and calling for emergency assistance) within the hospital room (e.g., hospital room 300), communication process 10 may process 408 at least a portion of the diction on a cloud-based computing resource (e.g., cloud resource 64) to identify at least one communication request within the hospital room (e.g., hospital room 300). As discussed above, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users.

If at least one communication request (e.g., placing a food/beverage order; requesting medication; contacting the nurse's station; and calling for emergency assistance) is detected, communication process 10 may establish 410 communication (e.g., via connection 308) between the hospital room (e.g., hospital room 300) and a remote location (e.g., nurse's station 310) within the hospital (e.g., hospital 312).

In order to effectuate such communication with the remote location (e.g., nurse's station 310), communication process 10 may interface 412 the virtual assistant (e.g., virtual assistant 32) with the remote location (e.g., nurse's station 310) within the hospital (e.g., hospital 312).

When interfacing 412 the virtual assistant (e.g., virtual assistant 32) with the remote location (e.g., nurse's station 310) within the hospital (e.g., hospital 312), communication process 10 may enable 414 functionality on the virtual assistant (e.g., virtual assistant 32) to effectuate cloud-based communication (e.g., via connection 308) between the virtual assistant (e.g., virtual assistant 32) and the remote location (e.g., nurse's station 310) within the hospital (e.g., hospital 312). For example, one or more applications (e.g., application 314) may be installed/executed on the virtual assistant (e.g., virtual assistant 32) to enable communication with the remote location (e.g., nurse's station 310) via communication process 10.

Communication process 10 may process 416 at least a portion of the diction to identify at least one supplemental command to be performed within the hospital room (e.g., hospital room 300), wherein the at least one supplemental command to be performed within the hospital room (e.g., hospital room 300) may include but are not limited to one or more of: controlling a hospital bed (e.g., hospital bed 302); controlling a room lighting system (e.g., lighting system 316); and controlling a television (e.g., television 306).

When processing 416 at least a portion of the diction to identify at least one supplemental command (e.g., controlling a hospital bed; controlling a room lighting system; and controlling a television) to be performed within the hospital room (e.g., hospital room 300), communication process 10 may process 418 at least a portion of the diction on a cloud-based computing resource (e.g., cloud resource 64) to identify at least one supplemental command (e.g., controlling a hospital bed; controlling a room lighting system; and controlling a television) to be performed within the hospital room (e.g., hospital room 300).

Enabling Hands Free, Voice-Based Control of a Hospital Bed

Figure 6:
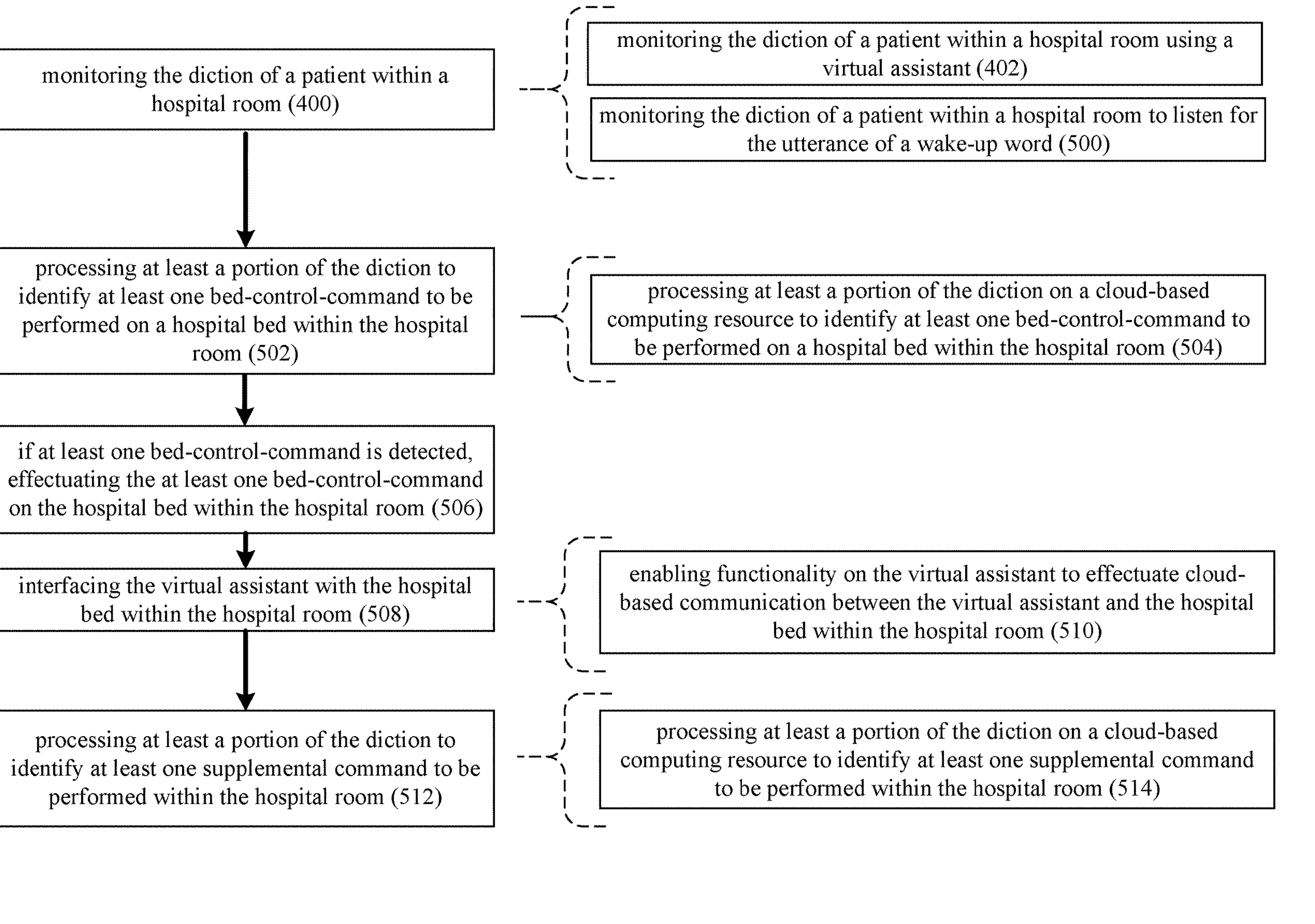
FIG. 6 is a flowchart of the communication process of FIG. 1 according to another embodiment of the present disclosure.

Referring also to FIG. 6, communication process 10 may monitor 400 the diction of a patient (e.g., patient 302) within a hospital room (e.g., hospital room 300). When monitoring 400 the diction of a patient (e.g., patient 302) within a hospital room (e.g., hospital room 300), communication process 10 may monitor 402 the diction of a patient (e.g., patient 302) within a hospital room (e.g., hospital room 300) using a virtual assistant (e.g., virtual assistant 32).

Additionally and when monitoring 400 the diction of a patient (e.g., patient 302) within a hospital room (e.g., hospital room 300), communication process 10 may monitor 500 the diction of a patient (e.g., patient 302) within a hospital room (e.g., hospital room 300) to listen for the utterance of a wake-up word. Examples of such wake-up words may include but are not limited to "Siri", "Alexa", "Google" and "Edera".

Communication process 10 may process 502 at least a portion of the diction to identify at least one bed-control-command to be performed on a hospital bed (e.g., hospital bed 304) within the hospital room (e.g., hospital room 300), wherein examples of such bed-control-commands to be performed on a hospital bed (e.g., hospital bed 304) within the hospital room (e.g., hospital room 300) may include but are not limited to one or more of: a head raise/lower bed-control-command; a knee raise/lower bed-control-command; a feet raise/lower bed-control-command; a bed raise/lower bed-control-command; a heater on/off bed-control-command; and a massager on/off bed-control-command.

Head Raise/Lower Bed-Control-Command: For example, patient (e.g., patient 302) may say "Hey Edera, Please raise my head".

Knee Raise/Lower Bed-Control-Command: For example, patient (e.g., patient 302) may say "Hey Edera, Please lower my knees".

Feet Raise/Lower Bed-Control-Command: For example, patient (e.g., patient 302) may say "Hey Edera, Please raise my feet".

Bed Raise/Lower Bed-Control-Command: For example, patient (e.g., patient 302) may say "Hey Edera, Please lift the bed".

Heater On/Off Bed-Control-Command: For example, patient (e.g., patient 302) may say "Hey Edera, Please turn on my bed heater".

Massager On/Off Bed-Control-Command: For example, patient (e.g., patient 302) may say "Hey Edera, Please turn on my bed messager".

In order to harness greater processing power, when processing 502 at least a portion of the diction to identify at least one bed-control-command (e.g., a head raise/lower bed-control-command; a knee raise/lower bed-control-command; a feet raise/lower bed-control-command; a bed raise/lower bed-control-command; a heater on/off bed-control-command; and a massager on/off bed-control-command) to be performed on a hospital bed (e.g., hospital bed 304) within the hospital room (e.g., hospital room 300), communication process 10 may process 504 at least a portion of the diction on a cloud-based computing resource (e.g., cloud resource 64) to identify at least one bed-control-command (e.g., a head raise/lower bed-control-command; a knee raise/lower bed-control-command; a feet raise/lower bed-control-command; a bed raise/lower bed-control-command; a heater on/off bed-control-command; and a massager on/off bed-control-command) to be performed on a hospital bed (e.g., hospital bed 304) within the hospital room (e.g., hospital room 300). As discussed above, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users.

If at least one bed-control-command (e.g., a head raise/lower bed-control-command; a knee raise/lower bed-control-command; a feet raise/lower bed-control-command; a bed raise/lower bed-control-command; a heater on/off bed-control-command; and a massager on/off bed-control-command) is detected, communication process 10 may effectuate 506 the at least one bed-control-command on the hospital bed (e.g., hospital bed 304) within the hospital room (e.g., hospital room 300).

In order to effectuate such communication with the hospital bed (e.g., hospital bed 304), communication process 10 may interface 508 the virtual assistant (e.g., virtual assistant 32) with the hospital bed (e.g., hospital bed 304) within the hospital room (e.g., hospital room 300).

When interfacing 508 the virtual assistant (e.g., virtual assistant 32) with the hospital bed (e.g., hospital bed 304) within the hospital room (e.g., hospital room 300), communication process 10 may enable 510 functionality on the virtual assistant (e.g., virtual assistant 32) to effectuate cloud-based communication between the virtual assistant (e.g., virtual assistant 32) and the hospital bed (e.g., hospital bed 304) within the hospital room (e.g., hospital room 300). For example, one or more applications (e.g., application 314) may be installed/executed on the virtual assistant (e.g., virtual assistant 32) to enable communication with the hospital bed (e.g., hospital bed 304) via communication process 10.

Communication process 10 may process 512 at least a portion of the diction to identify at least one supplemental command to be performed within the hospital room (e.g., hospital room 300), wherein examples of the at least one supplemental command to be performed within the hospital room (e.g., hospital room 300) may include but are not limited to one or more of: placing a food/beverage order; requesting medication; contacting the nurse's station (e.g., nurse's station 310); calling for emergency assistance; controlling a room lighting system (e.g., lighting system 316); and controlling a television (e.g., television 306).

When processing 512 at least a portion of the diction to identify at least one supplemental command (e.g., placing a food/beverage order; requesting medication; contacting the nurse's station; calling for emergency assistance; controlling a room lighting system; and controlling a television) to be performed within the hospital room (e.g., hospital room 300), communication process 10 may process 514 at least a portion of the diction on a cloud-based computing resource (e.g., cloud resource 64) to identify at least one supplemental command (e.g., placing a food/beverage order; requesting medication; contacting the nurse's station; calling for emergency assistance; controlling a room lighting system; and controlling a television) to be performed within the hospital room (e.g., hospital room 300).

While communication process 10 was discussed above as being utilized in a work environment and in a hospital environment, other configurations are possible. For example and as will be discussed below in greater detail, communication process 10 may be configured to provide assistance to users while they are in their homes.

Enabling Hands Free, Voice-Based Refills of Medications

Referring also to FIG. 7, communication process 10 may monitor 600 the diction of a prescription recipient (e.g., user 40) using a virtual assistant (e.g., virtual assistant 32). For this example, user 40 may be a recipient of a prescription (e.g., blood pressure medication) that is utilized on a long-term basis and is therefore repeatedly and frequently refilled.

Additionally and when monitoring 600 the diction of a prescription recipient (e.g., user 40) using a virtual assistant (e.g., virtual assistant 32), communication process 10 may monitor 602 the diction of a prescription recipient (e.g., user 40) using a virtual assistant (e.g., virtual assistant 32) to listen for the utterance of a wake-up word. Examples of such wake-up words may include but are not limited to "Ski", "Alexa", "Google" and "Edera".

Communication process 10 may process 604 at least a portion of the diction to identify at least one prescription refill task (e.g., task 66). One example of such a prescription refill task (e.g., task 66) may be the prescription recipient (e.g., user 40) using the virtual assistant (e.g., virtual assistant 32) to ask to have their blood pressure medication refilled.

When processing 604 at least a portion of the diction to identify at least one prescription refill task (e.g., task 66), communication process 10 may process 606 at least a portion of the diction using natural language processing. As discussed above, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

When processing 604 at least a portion of the diction to identify at least one prescription refill task (e.g., task 66), communication process 10 may also:

- process 608 at least a portion of the diction to identify one or more refill-indicative trigger words (e.g., "medicine", "prescription", "refill"); and
- process 610 at least a portion of the diction to identify one or more refill-indicative conversational structures (e.g., "can I have this filled", "I need more medicine?", "please refill my prescription").

The above-described refill-indicative trigger words and refill-indicative conversational structures may be manually defined or may be automatically defined. For example, an administrator of communication process 10 may manually define one or more lists (e.g., lists 58) that identify such refill-indicative trigger words and refill-indicative conversational structures. Additionally/alternatively, an administrator of communication process 10 may define seed data (e.g., seed data 60) that may be processed via artificial intelligence (AI) process 62 that may be configured to expand seed data 60 to define the above-referenced lists (e.g., lists 58).

In order to harness greater processing power, when processing 604 at least a portion of the diction to identify at least one prescription refill task (e.g., task 66), communication process 10 may process 612 at least a portion of the diction on a cloud-based computing resource to identify at least one prescription refill task (e.g., task 66). As discussed above, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users If at least one prescription refill task (e.g., task 66) is detected (e.g., user 40 asking to have their blood pressure medication refilled), communication process 10 may effectuate 606 the at least one prescription refill task (e.g., task 66) on a medical management system (e.g., medical management system 70), wherein examples of medical management system 70 may include but are not limited to one or more of: a medical office management system; a medical office billing system; and a pharmacy management system.

- Medical Office Management System: A medical office management system may be configured to enable medical professionals to manage a medical practice by e.g., scheduling appointments, scheduling staff, maintaining patient databases, maintaining patient electronic health records, issuing prescriptions, etc.
- Medical Office Billing System: A medical office billing system may be configured to enable medical professionals to manage accounts (e.g., account receivables and account payables) within a medical practice by e.g., enabling monetary inflows into the medical practice and enabling monetary outflows out of the medical practice.
- Pharmacy Management System: A pharmacy management system may be configured to enable pharmaceutical professionals to manage a pharmaceutical practice by e.g., processing prescriptions, ordering inventory, scheduling staff, maintaining client databases, maintaining client electronic pharmaceutical records, etc.

Accordingly, and as used in this disclosure, medical management system (e.g., medical management system 70) may include a management system and/or a billing system that is used in any type of medical establishment, example of which may include but are not limited to: a doctor's office, a medical practice, an urgent care facility, a long-term care facility, a rehabilitation facility, a nursing facility, a hospice care facility, a hospital facility/organization, a life sciences facility/organization, and a pharmacy facility/organization.

As will be discussed below, when effectuating 606 the at least one prescription refill task (e.g., task 66) on a medical management system (e.g., a medical office management system, a medical office billing system or a pharmacy management system), communication process 10 may parse 614 the at least one prescription refill task (e.g., task 66) into a plurality of subtasks; and effectuate 616 the plurality of subtasks (e.g., subtasks 68) on the medical management system (e.g., a medical office management system, a medical office billing system or a pharmacy management system).

For example and when effectuating 606 the at least one prescription refill task (e.g., task 66) on a medical management system (e.g., a medical office management system, a medical office billing system or a pharmacy management system), communication process 10 may identify 618 which prescription medication(s) are currently refillable by the prescription recipient (e.g., user 40). For example, assume that the prescription refill task (e.g., task 66) issued by the prescription recipient (e.g., user 40) was nonspecific (e.g., Please refill my prescription") and the prescription recipient (e.g., user 40) is currently receiving three prescription medications (e.g., a blood pressure medication, a cholesterol medication and an arthritis medication). Accordingly and when effectuating 606 the at least one prescription refill task (e.g., task 66) on a medical management system (e.g., a medical office management system, a medical office billing system or a pharmacy management system), communication process 10 may identify 618 these three prescription medication(s) that are currently refillable by the prescription recipient (e.g., user 40).

Further and when effectuating 606 the at least one prescription refill task (e.g., task 66) on a medical management system (e.g., a medical office management system, a medical office billing system or a pharmacy management system), communication process 10 may authenticate 620 the identity of the prescription recipient (e.g., user 40); ask 622 the prescription recipient (e.g., user 40) to define the specific medication to be refilled, thus defining a desired medication; and determine 624 if the desired medication is currently refillable. For example, communication process 10 may authenticate 620 the identity of the prescription recipient (e.g., user 40) using a voice print or via a PIN #/passcode; ask 622 the prescription recipient (e.g., user 40) to define the specific medication to be refilled, thus defining a desired medication (e.g., by selecting the blood pressure medication of the three medications that are refillable); and determine 624 if the desired medication is currently refillable (e.g., which may be determined by accessing the medical office management system and/or the pharmacy management system).

As is known in the art, a voice print is a digital model of the unique vocal characteristics of an individual. Voiceprints are created by specialized computer programs which process speech samples. The creation of a voiceprint is often referred to as "enrollment" in a biometric system. There are two general approaches to the creation and use of voiceprints. In traditional voice biometric systems that use classical machine learning algorithms, a voiceprint is created by performing "feature extraction" on one or more speech samples. This feature extraction process essentially creates personalized calculations or vectors related to specific attributes that make the user's speech unique. In these systems, feature extraction is also used to create a Universal Background Model or "UBM".

Additionally and when effectuating 606 the at least one prescription refill task (e.g., task 66) on a medical management system (e.g., a medical office management system, a medical office billing system or a pharmacy management system): if the desired medication (e.g., the blood pressure medication) is currently refillable, communication process 10 may effectuate 626 the refilling of the desired medication (e.g., the blood pressure medication) via the pharmacy management system; and notify 628 the prescription recipient (e.g., user 40) that the desired medication (e.g., the blood pressure medication) will be refilled.

Further and when effectuating 606 the at least one prescription refill task (e.g., task 66) on a medical management system (e.g., a medical office management system, a medical office billing system or a pharmacy management system): if the desired medication is not currently refillable, communication process 10 may engage 630 the medical management system to determine if the desired medication (e.g., the blood pressure medication) may be refilled for the prescription recipient (e.g., user 40). If the desired medication (e.g., the blood pressure medication) may be refilled for the prescription recipient (e.g., user 40), communication process 10 may effectuate 632 the refilling of the desired medication (e.g., the blood pressure medication) via a pharmacy management system and notify 634 the prescription recipient (e.g., user 40) that the desired medication (e.g., the blood pressure medication) will be refilled.

If the desired medication (e.g., the blood pressure medication) may not be refilled for the prescription recipient (e.g., user 40), communication process 10 may notify 636 the prescription recipient (e.g., user 40) that the desired medication (e.g., the blood pressure medication) will not be refilled.

As is known in the art, clinical research trials are utilized to gather clinical information concerning e.g., new drugs/processes/devices that are being tested in the marketplace. Unfortunately, one of the more difficult parts of such clinical research trials is gathering such clinical information from the trial participants. As will be discussed below in greater detail, communication process 10 may be configured to provide assistance with respect to gathering such clinical information from the trial participants.

Enabling Hands Free, Voice-Based Survey Responses Via a Secure VA

Referring also to FIG. 8, communication process 10 may interface 700 a clinical research system (e.g., clinical research system 72) with a virtual assistant (e.g., virtual assistant 32) accessible by a clinical trial participant (e.g., user 40). Examples of the clinical research system (e.g., clinical research system 72) may include a system that allows for the implementation of such clinical research trials and the gathering of such clinical information from the trial participants (e.g., user 40). For this example, assume that the trial participant (e.g., user 40) is involved in a clinical trial for the blood pressure medication that that they are taking.

When interfacing 700 a clinical research system (e.g., clinical research system 72) with a virtual assistant (e.g., virtual assistant 32) accessible by a clinical trial participant (e.g., user 40), communication process 10 may enable 702 functionality on the virtual assistant (e.g., virtual assistant 32) to effectuate cloud-based communication between the virtual assistant (e.g., virtual assistant 32) and the clinical research system (e.g., clinical research system 72). For example, one or more applications (e.g., application 74) may be installed/executed on the virtual assistant (e.g., virtual assistant 32) to enable communication with the clinical research system (e.g., clinical research system 72) via communication process 10.

Communication process 10 may provide 704 a clinical research survey (e.g., clinical research survey 76) to the clinical trial participant (e.g., user 40) via the virtual assistant (e.g., virtual assistant 32), wherein the clinical research survey (e.g., clinical research survey 76) may define one or more questions (e.g., questions 78). Examples of such questions (e.g., questions 78) may include questions concerning the efficacy of the blood pressure medication and the side effects of the blood pressure medication.

When providing 704 a clinical research survey (e.g., clinical research survey 76) to the clinical trial participant (e.g., user 40) via the virtual assistant (e.g., virtual assistant 32), communication process 10 may utilize 706 text-to-speech technology to generate one or more speech-based questions based, at least in part, upon the one or more questions (e.g., questions 78) defined within the clinical research survey (e.g., clinical research survey 76).

As is known in the art, a text-to-speech (TTS) system converts normal language text into speech and is composed of two parts: a front-end and a back-end. The front-end has two major tasks. First, it converts raw text containing symbols like numbers and abbreviations into the equivalent of written-out words. This process is often called text normalization, pre-processing, or tokenization. The front-end then assigns phonetic transcriptions to each word, and divides and marks the text into prosodic units, like phrases, clauses, and sentences. The process of assigning phonetic transcriptions to words is called text-to-phoneme or grapheme-to-phoneme conversion. Phonetic transcriptions and prosody information together make up the symbolic linguistic representation that is output by the front-end. The back-end—often referred to as the synthesizer—then converts the symbolic linguistic representation into sound. In certain systems, this part includes the computation of the target prosody (pitch contour, phoneme durations), which is then imposed on the output speech.

When providing 704 a clinical research survey (e.g., clinical research survey 76) to the clinical trial participant (e.g., user 40) via the virtual assistant (e.g., virtual assistant 32), communication process 10 may notify 708 the clinical trial participant (e.g., user 40) of the availability of the clinical research survey (e.g., clinical research survey 76). For example, communication process 10 may notify 708 the clinical trial participant (e.g., user 40) of the availability of clinical research survey 76 by e.g., having virtual assistant 32 make a unique sound or flash a unique light. Additionally/alternatively, communication process 10 may notify 708 the clinical trial participant (e.g., user 40) of the availability of clinical research survey 76 by sending user 40 a text message or an email.

When providing 704 a clinical research survey (e.g., clinical research survey 76) to the clinical trial participant (e.g., user 40) via the virtual assistant (e.g., virtual assistant 32), communication process 10 may confirm 710 the identity of the clinical trial participant (e.g., user 40) before enabling the clinical trial participant (e.g., user 40) to respond to the clinical research survey (e.g., clinical research survey 76). For example, communication process 10 may confirm 710 the identity of the clinical trial participant (e.g., user 40) using a voice print or via a PIN #/passcode.

As discussed above, a voice print is a digital model of the unique vocal characteristics of an individual. Voiceprints are created by specialized computer programs which process speech samples. The creation of a voiceprint is often referred to as "enrollment" in a biometric system. There are two general approaches to the creation and use of voiceprints. In traditional voice biometric systems that use classical machine learning algorithms, a voiceprint is created by performing "feature extraction" on one or more speech samples. This feature extraction process essentially creates personalized calculations or vectors related to specific attributes that make the user's speech unique. In these systems, feature extraction is also used to create a Universal Background Model or "UBM".

When providing 704 a clinical research survey (e.g., clinical research survey 76) to the clinical trial participant (e.g., user 40) via the virtual assistant (e.g., virtual assistant 32), communication process 10 may provide 712 one or more speech-based questions based, at least in part, upon the clinical research survey (e.g., clinical research survey 76) to the clinical trial participant (e.g., user 40) so that the clinical trial participant (e.g., user 40) may provide a speech-based answer as part of the survey response. For example, clinical research survey 76 may include a plurality of text-based questions (e.g., questions 78), wherein communication process 10 may utilize text-to-speech technology to generate speech-based questions from these text-based questions. Communication process 10 may then provide 712 these speech-based questions to the clinical trial participant (e.g., user 40) so that the clinical trial participant (e.g., user 40) may provide a speech-based answer as part of a survey response (e.g., survey response 80).

Additionally/alternatively, the virtual assistant (e.g., virtual assistant 32) may include a display screen (not shown) that allows for the displaying of text & images. An example of such a virtual assistant may include but is not limited to an Amazon Show™ device. Accordingly and in such a configuration, when providing 704 a clinical research survey (e.g., clinical research survey 76) to the clinical trial participant (e.g., user 40) via the virtual assistant (e.g., virtual assistant 32), communication process 10 may render one or more text-based questions on the display screen (not shown) of the virtual assistant (e.g., virtual assistant 32), wherein these one or more text-based questions may be based, at least in part, upon the one or more questions (e.g., questions 78) defined within the clinical research survey (e.g., clinical research survey 76).

Communication process 10 may receive 714 the survey response (e.g., survey response 80) to the clinical research survey (e.g., clinical research survey 76) from the clinical trial participant (e.g., user 40) via the virtual assistant (e.g., virtual assistant 32), wherein the survey response (e.g., survey response 80) defines one or more answers (e.g., answers 82) to the one or more questions (e.g., questions 78) defined within the clinical research survey (e.g., clinical research survey 76).

When receiving 714 a survey response (e.g., survey response 80) to the clinical research survey (e.g., clinical research survey 76) from the clinical trial participant (e.g., user 40) via the virtual assistant (e.g., virtual assistant 32), communication process 10 may process 716 at least a portion of the survey response (e.g., survey response 80) using natural language processing.

As discussed above, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

When receiving 714 a survey response (e.g., survey response 80) to the clinical research survey (e.g., clinical research survey 76) from the clinical trial participant (e.g., user 40) via the virtual assistant (e.g., virtual assistant 32), communication process 10 may receive 718 one or more speech-based answers from the clinical trial participant (e.g., user 40) as part of the survey response (e.g., survey response 80). For example, communication process 10 may provide the clinical trial participant (e.g., user 40) with speech-based questions that are based upon the text-based questions (e.g., questions 78) included within clinical research survey 76. The clinical trial participant (e.g., user 40) may then provide speech-based answers as part of the survey response (e.g., survey response 80).

When receiving 714 a survey response (e.g., survey response 80) to the clinical research survey (e.g., clinical research survey 76) from the clinical trial participant (e.g., user 40) via the virtual assistant (e.g., virtual assistant 32), communication process 10 may generate 720 one or more text-based answers (e.g., answers 82) from the one or more speech-based answers received from the clinical trial participant (e.g., user 40) as part of the survey response (e.g., survey response 80).

As is known in the art, speech recognition is an interdisciplinary subfield of computer science and computational linguistics that develops methodologies and technologies that enable the recognition and translation of spoken language into text by computers with the main benefit of searchability. It is also known as automatic speech recognition (ASR), computer speech recognition or speech to text (STT). It incorporates knowledge and research in the computer science, linguistics and computer engineering fields. The reverse process is speech synthesis. Some speech recognition systems require "training" (also called "enrollment") where an individual speaker reads text or isolated vocabulary into the system. The system analyzes the person's specific voice and uses it to fine-tune the recognition of that person's speech, resulting in increased accuracy. Systems that do not use training are called "speaker-independent" systems. Systems that use training are called "speaker dependent".

As discussed above, the virtual assistant (e.g., virtual assistant 32) may include a display screen (not shown) that allows for the displaying of text & images. An example of such a virtual assistant may include but is not limited to an Amazon Show™ device. Accordingly and in such a configuration, when receiving 714 a survey response (e.g., survey response 80) to the clinical research survey (e.g., clinical research survey 76) from the clinical trial participant (e.g., user 40) via the virtual assistant (e.g., virtual assistant 32), communication process 10 may enable the clinical trial participant (e.g., user 40) to type out responses on the display screen (not shown) of the virtual assistant (e.g., virtual assistant 32).

Additionally, communication process 10 may require the clinical trial participant (e.g., user 40) to provide/upload information from a personal medical device if required by the clinical research survey (e.g., clinical research survey 76). For example, if the clinical research survey (e.g., clinical research survey 76) concerns the efficacy of a drug to control blood sugar, communication process 10 may require the clinical trial participant (e.g., user 40) to upload information from their personal blood glucose monitor.

When receiving 714 a survey response (e.g., survey response 80) to the clinical research survey (e.g., clinical research survey 76) from the clinical trial participant (e.g., user 40) via the virtual assistant (e.g., virtual assistant 32), communication process 10 may associate 722 the one or more text-based answers (e.g., one or more of answers 82) with the one or more questions (e.g., questions 78) defined within the clinical research survey (e.g., clinical research survey 76). Accordingly, communication process 10 may e.g., associate 722 Answer #1 (e.g., included within answers 82) with Question #1 (e.g., included within questions 78), and may associate 722 Answer #2 (e.g., included within answers 82) with Question #2 (e.g., included within questions 78), and so on.

As will be discussed below in greater detail, communication process 10 may be configure to allow for the utilization of a generic virtual assistant (e.g., virtual assistant 32) by a medical management system (e.g., medical management system 70) to automate the processing of redundant and/or time-consuming tasks.

Figure 9:
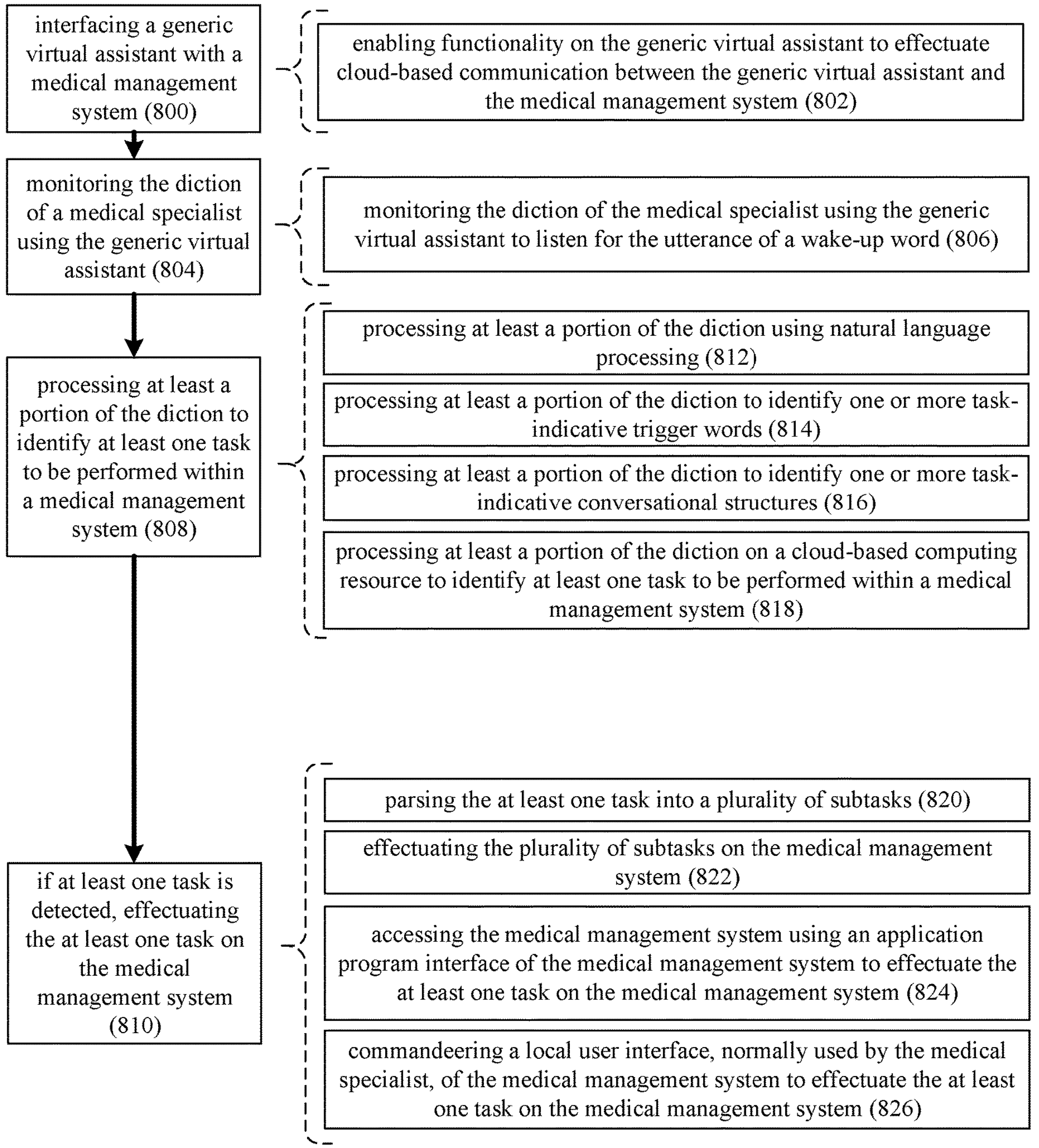
FIG. 9 is a flowchart of the communication process of FIG. 1 according to another embodiment of the present disclosure.

Using a Generic VA to Interface with Medical Office/Pharmacy Management Software Referring also to FIG. 9, communication process 10 may interface 800 a generic virtual assistant (e.g., virtual assistant 32) with a medical management system (e.g., medical management system 70), wherein examples of medical management system 70 may include but are not limited to one or more of: a medical office management system; a medical office billing system; and a pharmacy management system

- Medical Office Management System: A medical office management system may be configured to enable medical professionals to manage a medical practice by e.g., scheduling appointments, scheduling staff, maintaining patient databases, maintaining patient electronic health records, issuing prescriptions, etc.

Medical Office Billing System: A medical office billing system may be configured to enable medical professionals to manage accounts (e.g., account receivables and account payables) within a medical practice by e.g., enabling monetary inflows into the medical practice and enabling monetary outflows out of the medical practice.

Pharmacy Management System: A pharmacy management system may be configured to enable pharmaceutical professionals to manage a pharmaceutical practice by e.g., processing prescriptions, ordering inventory, scheduling staff, maintaining client databases, maintaining client electronic pharmaceutical records, etc.

As discussed above, medical management system (e.g., medical management system 70) may include a management system and/or a billing system that is used in any type of medical establishment, example of which may include but are not limited to: a doctor's office, a medical practice, an urgent care facility, a long-term care facility, a rehabilitation facility, a nursing facility, a hospice care facility, a hospital facility/organization, a life sciences facility/organization, and a pharmacy facility/organization.

When interfacing 800 a generic virtual assistant (e.g., virtual assistant 32) with a medical management system (e.g., medical management system 70), communication process 10 may enable 802 functionality on the generic virtual assistant (e.g., virtual assistant 32) to effectuate cloud-based communication between the generic virtual assistant (e.g., virtual assistant 32) and the medical management system (e.g., medical management system 70). For example, one or more applications (e.g., application 74) may be installed/executed on the virtual assistant (e.g., virtual assistant 32) to enable communication with the medical management system (e.g., medical management system 70) via communication process 10.

Communication process 10 may monitor 804 the diction of a medical specialist (e.g., user 40) using the generic virtual assistant (e.g., virtual assistant 32). For example and when monitoring 804 the diction of a medical specialist (e.g., user 40) using the generic virtual assistant (e.g., virtual assistant 32), communication process 10 may monitor 806 the diction of the medical specialist (e.g., user 40) using the generic virtual assistant (e.g., virtual assistant 32) to listen for the utterance of a wake-up word. Examples of such wake-up words may include but are not limited to "Ski", "Alexa", "Google" and "Edera".

The medical specialist (e.g., user 40) utilizing the generic virtual assistant (e.g., virtual assistant 32) may be one of many different professionals that work in the medical field. Accordingly and when monitoring 804 the diction of a medical specialist (e.g., user 40) using the generic virtual assistant (e.g., virtual assistant 32), communication process 10 may include one or more of the following:

monitor 804 the diction of a claim processing specialist (e.g., user 40) using the generic virtual assistant (e.g., virtual assistant 32), wherein a claim processing specialist may e.g., process insurance claims within a medical office for submission to insurance companies. For example, a claim processing specialist may say "Hey Edera, please submit a claim to Insurance Company X for a CAT Scan for Patient Mary Jones".

monitor 804 the diction of a billing specialist (e.g., user 40) using the generic virtual assistant (e.g., virtual assistant 32), wherein a billing specialist may e.g., process account payable invoices to effectuate billing and process account receivable invoices to effectuate payment. For example, a billing specialist may say "Hey Edera, please generate and submit an invoice to Patient Mary Jones for a $100 CAT Scan copay".

monitor 804 the diction of a data processing specialist (e.g., user 40) using the generic virtual assistant (e.g., virtual assistant 32), wherein a data processing specialist may e.g., generate & update data records. For example, a data processing specialist may say "Hey Edera, please update the contact phone number for Patient Mary Jones to 123-456-7890".

monitor 804 the diction of an ordering specialist (e.g., user 40) using the generic virtual assistant (e.g., virtual assistant 32), wherein an ordering specialist may e.g., effectuate the ordering of supplies and the ordering of medical procedures. For example, a data processing specialist may say "Hey Edera, please order a CAT Scan for Patient Mary Jones".

Communication process 10 may process 808 at least a portion of the diction to identify at least one task (e.g., task 66) to be performed within a medical management system (e.g., medical management system 70); and if at least one task (e.g., task 66) is detected, communication process 10 may effectuate 810 the at least one task (e.g., task 66) on the medical management system (e.g., medical management system 70).

When processing 808 at least a portion of the diction to identify at least one task (e.g., task 66) to be performed within a medical management system (e.g., medical management system 70), communication process 10 may process 812 at least a portion of the diction using natural language processing. As discussed above, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

When processing 808 at least a portion of the diction to identify at least one task (e.g., task 66) to be performed within a medical management system (e.g., medical management system 70), communication process 10 may also:

process 814 at least a portion of the diction to identify one or more task-indicative trigger words (e.g., "submit", "claim", "generate", "update", "order"); and process 816 at least a portion of the diction to identify one or more task-indicative conversational structures (e.g., "please bill", "I need to update", "submit this invoice").

The above-described task-indicative trigger words, and task-indicative conversational structures may be manually defined or may be automatically defined. For example, an administrator of communication process 10 may manually define one or more lists (e.g., lists 58) that identify such task-indicative trigger words, and task-indicative conversational structures. Additionally/alternatively, an administrator of communication process 10 may define seed data (e.g., seed data 60) that may be processed via artificial intelligence (AI) process 62 that may be configured to expand seed data 60 to define the above-referenced lists (e.g., lists 58).

When processing 808 at least a portion of the diction to identify at least one task (e.g., task 66) to be performed within a medical management system (e.g., medical management system 70), communication process 10 may process 818 at least a portion of the diction on a cloud-based computing resource (e.g., cloud resource 64) to identify at least one task (e.g., task 66) to be performed within a medical management system (e.g., medical management system 70). As is known in the art, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users.

When effectuating 810 the at least one task (e.g., task 66) on the medical management system (e.g., medical management system 70), communication process 10 may parse 820 the at least one task (e.g., task 66) into a plurality of subtasks (e.g., subtasks 68); and effectuate 822 the plurality of subtasks (e.g., subtasks 68) on the medical management system (e.g., medical management system 70). For example, in order to accomplish task 66, communication process 10 may effectuate a plurality of discrete subtasks (e.g., subtasks 68), examples of which may include but are not limited to identifying any outstanding balance owed by Patient Mary Jones, incrementing that amount by a $100 copay for the ordered CAT Scan, generating an invoice for that incremented amount, and submitting that invoice to Patient Mary Jones.

Further and when effectuating 810 the at least one task (e.g., task 66) on the medical management system (e.g., medical management system 70): communication process 10 may access 824 the medical management system (e.g., medical management system 70) using an application program interface (e.g., API 84) of the medical management system (e.g., medical management system 70) to effectuate the at least one task (e.g., task 66) on the medical management system (e.g., medical management system 70).

As is known in the art, an application programming interface (API) is a way for two or more computer programs to communicate with each other. It is a type of software interface, offering a service to other pieces of software. A document or standard that describes how to build or use such a connection or interface is called an API specification. A computer system that meets this standard is said to implement or expose an API. The term API may refer either to the specification or to the implementation.

Additionally/alternatively and when effectuating 810 the at least one task (e.g., task 66) on the medical management system (e.g., medical management system 70): communication process 10 may commandeer 826 a local user interface (e.g., user interface 86), normally used by the medical specialist (e.g., user 40), of the medical management system (e.g., medical management system 70) to effectuate the at least one task on the medical management system (e.g., medical management system 70). Accordingly and is such a situation, when communication process 10 is effectuating 810 the at least one task (e.g., task 66) on the medical management system (e.g., medical management system 70), the medical specialist (e.g., user 40) may watch what appears to be remote manipulation of their local user interface (e.g., user interface 86) that they use to access the medical management system (e.g., medical management system 70).

Enabling Hands Free, Voice-Based Automation of Tasks

Figure 10:
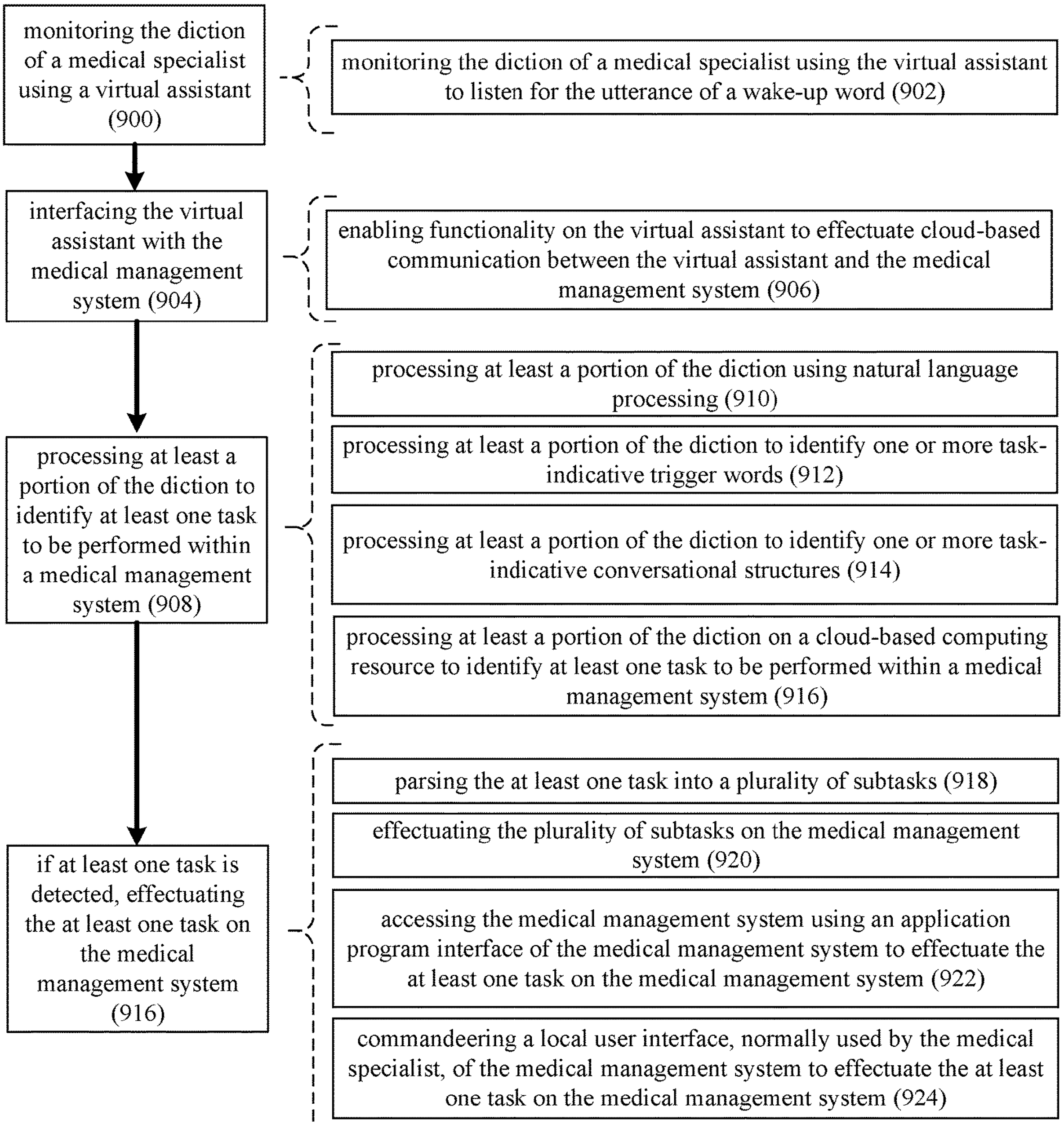
FIG. 10 is a flowchart of the communication process of FIG. 1 according to another embodiment of the present disclosure.

Referring also to FIG. 10, communication process 10 may monitor 900 the diction of a medical specialist (e.g., user 40) using a virtual assistant (e.g., virtual assistant 32). For example and when monitoring 900 the diction of a medical specialist (e.g., user 40) using a virtual assistant (e.g., virtual assistant 32), communication process 10 may monitor 902 the diction of a medical specialist (e.g., user 40) using a virtual assistant (e.g., virtual assistant 32) to listen for the utterance of a wake-up word. Examples of such wake-up words may include but are not limited to "Siri", "Alexa", "Google" and "Edera".

As discussed above, the medical specialist (e.g., user 40) utilizing communication process 10 may be one of many different professionals that work in the medical field. Accordingly and when monitoring 900 the diction of a medical specialist (e.g., user 40) using the virtual assistant (e.g., virtual assistant 32), communication process 10 may include one or more of the following:

- monitor 900 the diction of a claim processing specialist (e.g., user 40) using the virtual assistant (e.g., virtual assistant 32), wherein a claim processing specialist may e.g., process insurance claims within a medical office for submission to insurance companies. For example, a claim processing specialist may say "Hey Edera, please submit a claim to Insurance Company X for a CAT Scan for Patient Mary Jones".
- monitor 900 the diction of a billing specialist (e.g., user 40) using the virtual assistant (e.g., virtual assistant 32), wherein a billing specialist may e.g., process account payable invoices to effectuate billing and process account receivable invoices to effectuate payment. For example, a billing specialist may say "Hey Edera, please generate and submit an invoice to Patient Mary Jones for a $100 CAT Scan copay".
- monitor 900 the diction of a data processing specialist (e.g., user 40) using the virtual assistant (e.g., virtual assistant 32), wherein a data processing specialist may e.g., generate & update data records. For example, a data processing specialist may say "Hey Edera, please update the contact phone number for Patient Mary Jones to 123-456-7890".
- monitor 900 the diction of an ordering specialist (e.g., user 40) using the virtual assistant (e.g., virtual assistant 32), wherein an ordering specialist may e.g., effectuate the ordering of supplies and the ordering of medical procedures. For example, a data processing specialist may say "Hey Edera, please order a CAT Scan for Patient Mary Jones".

The above-described list is intended to be illustrative and not all inclusive. Accordingly, other configurations are possible and are considered to be within the scope of this disclosure. Communication process 10 may interface 904 the virtual assistant (e.g., virtual assistant 32) with the medical management system (e.g., medical management system 70). For example and when interfacing 904 the virtual assistant (e.g., virtual assistant 32) with a medical management system (e.g., medical management system 70), communication process 10 may enable 906 functionality on the virtual assistant (e.g., virtual assistant 32) to effectuate cloud-based communication between the virtual assistant (e.g., virtual assistant 32) and the medical management system (e.g., medical management system 70). For example, one or more applications (e.g., application 74) may be installed/executed on the virtual assistant (e.g., virtual assistant 32) to enable communication with the medical management system (e.g., medical management system 70) via communication process 10.

Communication process 10 may process 908 at least a portion of the diction to identify at least one task (e.g., task

66) to be performed within a medical management system (e.g., medical management system 70), wherein examples of medical management system 70 may include but are not limited to one or more of: a medical office management system; a medical office billing system; and a pharmacy management system.

Medical Office Management System: A medical office management system may be configured to enable medical professionals to manage a medical practice by e.g., scheduling appointments, scheduling staff, maintaining patient databases, maintaining patient electronic health records, issuing prescriptions, etc.

Medical Office Billing System: A medical office billing system may be configured to enable medical professionals to manage accounts (e.g., account receivables and account payables) within a medical practice by e.g., enabling monetary inflows into the medical practice and enabling monetary outflows out of the medical practice. Pharmacy Management System: A pharmacy management system may be configured to enable pharmaceutical professionals to manage a pharmaceutical practice by e.g., processing prescriptions, ordering inventory, scheduling staff, maintaining client databases, maintaining client electronic pharmaceutical records, etc.

As discussed above, medical management system (e.g., medical management system 70) may include a management system and/or a billing system that is used in any type of medical establishment, example of which may include but are not limited to: a doctor's office, a medical practice, an urgent care facility, a long-term care facility, a rehabilitation facility, a nursing facility, a hospice care facility, a hospital facility/organization, a life sciences facility/organization, and a pharmacy facility/organization.

When processing 908 at least a portion of the diction to identify at least one task (e.g., task 66) to be performed within a medical management system (e.g., medical management system 70), communication process 10 may process 910 at least a portion of the diction using natural language processing. As discussed above, natural language processing is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology can then accurately extract information and insights contained in the documents as well as categorize and organize the documents themselves.

When processing 908 at least a portion of the diction to identify at least one task (e.g., task 66) to be performed within a medical management system (e.g., medical management system 70), communication process 10 may also:

process 912 at least a portion of the diction to identify one or more task-indicative trigger words (e.g., "submit", "claim", "generate", "update", "order"); and process 914 at least a portion of the diction to identify one or more task-indicative conversational structures (e.g., "please bill", "I need to update", "submit this invoice").

The above-described task-indicative trigger words, and task-indicative conversational structures may be manually defined or may be automatically defined. For example, an administrator of communication process 10 may manually define one or more lists (e.g., lists 58) that identify such task-indicative trigger words, and task-indicative conversational structures. Additionally/alternatively, an administrator of communication process 10 may define seed data (e.g., seed data 60) that may be processed via artificial intelligence (AI) process 62 that may be configured to expand seed data 60 to define the above-referenced lists (e.g., lists 58).

When processing 908 at least a portion of the diction to identify at least one task (e.g., task 66) to be performed within a medical management system (e.g., medical management system 70), communication process 10 may process 916 at least a portion of the diction on a cloud-based computing resource to identify at least one task (e.g., task 66) to be performed within a medical management system (e.g., medical management system 70). As discussed above, cloud computing is the on-demand availability of computer system resources, especially data storage (cloud storage) and computing power, without direct active management by the user. Large clouds often have functions distributed over multiple locations, each location being a data center. Cloud computing relies on sharing of resources to achieve coherence and typically using a "pay-as-you-go" model which can help in reducing capital expenses but may also lead to unexpected operating expenses for unaware users.

If at least one task (e.g., task 66) is detected, communication process 10 may effectuate 916 the at least one task (e.g., task 66) on the medical management system (e.g., medical management system 70).

When effectuating 916 the at least one task (e.g., task 66) on the medical management system (e.g., medical management system 70), communication process 10 may parse 918 the at least one task (e.g., task 66) into a plurality of subtasks (e.g., subtasks 68); and effectuate 920 the plurality of subtasks (e.g., subtasks 68) on the medical management system (e.g., medical management system 70). For example, in order to accomplish task 66, communication process 10 may effectuate a plurality of discrete subtasks (e.g., subtasks 68), examples of which may include but are not limited to identifying any outstanding balance owed by Patient Mary Jones, incrementing that amount by a $100 copay for the ordered CAT Scan, generating an invoice for that incremented amount, and submitting that invoice to Patient Mary Jones.

Further and when effectuating 916 the at least one task (e.g., task 66) on the medical management system (e.g., medical management system 70): communication process 10 may access 922 the medical management system (e.g., medical management system 70) using an application program interface (e.g., API 84) of the medical management system (e.g., medical management system 70) to effectuate the at least one task (e.g., task 66) on the medical management system (e.g., medical management system 70).

As is known in the art, an application programming interface (API) is a way for two or more computer programs to communicate with each other. It is a type of software interface, offering a service to other pieces of software. A document or standard that describes how to build or use such a connection or interface is called an API specification. A computer system that meets this standard is said to implement or expose an API. The term API may refer either to the specification or to the implementation.

Additionally/alternatively and when effectuating 916 the at least one task (e.g., task 66) on the medical management system (e.g., medical management system 70): communication process 10 may commandeer 924 a local user interface (e.g., user interface 86), normally used by the medical specialist (e.g., user 40), of the medical management system (e.g., medical management system 70) to effectuate the at least one task (e.g., task 66) on the medical management system (e.g., medical management system 70).

Accordingly and is such a situation, when communication process 10 is effectuating 916 the at least one task (e.g., task 66) on the medical management system (e.g., medical management system 70), the medical specialist (e.g., user 40) may watch what appears to be remote manipulation of their local user interface (e.g., user interface 86) that they use to access the medical management system (e.g., medical management system 70).

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:

monitoring diction of a patient within a hospital room using a virtual assistant, wherein the virtual assistant is a client electronic device including a display screen;

processing at least a portion of the diction to identify at least one bed-control-command to be performed on a hospital bed within the hospital room;

in response to detecting at least one bed-control-command, effectuating the at least one bed-control-command on the hospital bed within the hospital room, wherein the at least one bed-control-command includes a massager on/off bed-control-command, wherein effectuating the at least one bed-control-command includes:

communicating the massager on/off bed-control-command from the virtual assistant to the hospital bed using an application executed on the virtual assistant to communicate with the hospital bed, and performing the massager on/off bed-control-command within the hospital bed in response to processing the massager on/off bed-control-command communicated by the virtual assistant;

processing the at least a portion of the diction to identify at least one supplemental command to be performed within the hospital room, wherein the at least one supplemental command includes a prescription refill task based upon, at least in part, the detection of a refill-indicative trigger word from a list of predefined refill-indicative trigger words, wherein the list of predefined refill-indicative trigger words is generated using an artificial intelligence (AI) process that expands seed data associated with a subset of refill-indicative trigger words into a plurality of refill-indicative trigger words for populating the list of predefined refill-indicative trigger words; and in response to detecting the prescription refill task:

authenticating the patient using a voice print associated with the patient;

prompting the patient, using the virtual assistant, for a prescription to refill;

determining that the prescription to refill is currently refillable; and effectuating the prescription refill task, using the virtual assistant, by communicating with a medical management system.

2. The computer-implemented method of claim 1, further comprising:

interfacing the virtual assistant with the hospital bed within the hospital room.

3. The computer-implemented method of claim 2, wherein interfacing the virtual assistant with the hospital bed within the hospital room includes:

enabling functionality on the virtual assistant to effectuate cloud-based communication between the virtual assistant and the hospital bed within the hospital room.

4. The computer-implemented method of claim 1, wherein monitoring the diction of the patient within the hospital room includes:

monitoring the diction of the patient within the hospital room to listen for utterance of a wake-up word.

5. The computer-implemented method of claim 1, wherein processing the at least a portion of the diction to identify the at least one bed-control-command to be performed on the hospital bed within the hospital room includes:

processing the at least a portion of the diction on a cloud-based computing resource to identify at least one bed-control-command to be performed on the hospital bed within the hospital room.

6. The computer-implemented method of claim 1, wherein the at least one bed-control-command to be performed on the hospital bed within the hospital room includes one or more of:

a head raise/lower bed-control-command;

a knee raise/lower bed-control-command;

a feet raise/lower bed-control-command;

a bed raise/lower bed-control-command; and a heater on/off bed-control-command.

7. The computer-implemented method of claim 1, wherein processing the at least a portion of the diction to identify the at least one supplemental command to be performed within the hospital room includes:

processing the at least a portion of the diction on a cloud-based computing resource to identify the at least one supplemental command to be performed within the hospital room.

8. The computer-implemented method of claim 1, wherein the at least one supplemental command to be performed within the hospital room includes one or more of:

placing a food/beverage order;

contacting a nurse's station;

calling for emergency assistance;

controlling a room lighting system; and controlling a television.

9. A computer program product residing on a non-transitory computer readable medium having a plurality of instructions stored thereon which, when executed by a processor, cause the processor to perform operations comprising:

monitoring diction of a patient within a hospital room using a virtual assistant, wherein the virtual assistant is a client electronic device including a display screen;

processing at least a portion of the diction to identify at least one bed-control-command to be performed on a hospital bed within the hospital room;

in response to detecting at least one bed-control-command, effectuating the at least one bed-control-command on the hospital bed within the hospital room, wherein the at least one bed-control-command includes a massager on/off bed-control-command, wherein effectuating the at least one bed-control-command includes:

communicating the massager on/off bed-control-command from the virtual assistant to the hospital bed using an application executed on the virtual assistant to communicate with the hospital bed, and performing the massager on/off bed-control-command within the hospital bed in response to processing the massager on/off bed-control-command communicated by the virtual assistant;

processing the at least a portion of the diction to identify at least one supplemental command to be performed within the hospital room, wherein the at least one supplemental command includes a prescription refill task based upon, at least in part, the detection of a refill-indicative trigger word from a list of predefined refill-indicative trigger words, wherein the list of predefined refill-indicative trigger words is generated using an artificial intelligence (AI) process that expands seed data associated with a subset of refill-indicative trigger words into a plurality of refill-indicative trigger words for populating the list of predefined refill-indicative trigger words; and in response to detecting the prescription refill task:

authenticating the patient using a voice print associated with the patient;

prompting the patient, using the virtual assistant, for a prescription to refill;

determining that the prescription to refill is currently refillable; and effectuating the prescription refill task, using the virtual assistant, by communicating with a medical management system.

10. The computer program product of claim 9, further comprising:

interfacing the virtual assistant with the hospital bed within the hospital room.

11. The computer program product of claim 10, wherein interfacing the virtual assistant with the hospital bed within the hospital room includes:

enabling functionality on the virtual assistant to effectuate cloud-based communication between the virtual assistant and the hospital bed within the hospital room.

12. The computer program product of claim 9, wherein monitoring the diction of the patient within the hospital room includes:

monitoring the diction of the patient within the hospital room to listen for utterance of a wake-up word.

13. The computer program product of claim 9, wherein processing the at least a portion of the diction to identify the at least one bed-control-command to be performed on the hospital bed within the hospital room includes:

processing the at least a portion of the diction on a cloud-based computing resource to identify at least one bed-control-command to be performed on the hospital bed within the hospital room.

14. The computer program product of claim 9, wherein the at least one bed-control-command to be performed on the hospital bed within the hospital room includes one or more of:

a head raise/lower bed-control-command;

a knee raise/lower bed-control-command;

a feet raise/lower bed-control-command;

a bed raise/lower bed-control-command; and a heater on/off bed-control-command.

15. The computer program product of claim 9, wherein processing the at least a portion of the diction to identify the at least one supplemental command to be performed within the hospital room includes:

processing the at least a portion of the diction on a cloud-based computing resource to identify the at least one supplemental command to be performed within the hospital room.

16. The computer program product of claim 9, wherein the at least one supplemental command to be performed within the hospital room includes one or more of:

placing a food/beverage order;

requesting medication;

contacting a nurse's station;

calling for emergency assistance;

controlling a room lighting system; and controlling a television.

17. A computing system including a processor and memory configured to perform operations comprising:

monitoring diction of a patient within a hospital room using a virtual assistant, wherein the virtual assistant is a client electronic device including a display screen;

processing at least a portion of the diction to identify at least one bed-control-command to be performed on a hospital bed within the hospital room;

in response to detecting at least one bed-control-command, effectuating the at least one bed-control-command on the hospital bed within the hospital room, wherein the at least one bed-control-command includes a massager on/off bed-control-command, wherein effectuating the at least one bed-control-command includes:

communicating the massager on/off bed-control-command from the virtual assistant to the hospital bed using an application executed on the virtual assistant to communicate with the hospital bed, and performing the massager on/off bed-control-command within the hospital bed in response to processing the massager on/off bed-control-command communicated by the virtual assistant;

processing the at least a portion of the diction to identify at least one supplemental command to be performed within the hospital room, wherein the at least one supplemental command includes a prescription refill task based upon, at least in part, the detection of a refill-indicative trigger word from a list of predefined refill-indicative trigger words, wherein the list of predefined refill-indicative trigger words is generated using an artificial intelligence (AI) process that expands seed data associated with a subset of refill-indicative trigger words into a plurality of refill-indicative trigger words for populating the list of predefined refill-indicative trigger words; and in response to detecting the prescription refill task:

authenticating the patient using a voice print associated with the patient;

prompting the patient, using the virtual assistant, for a prescription to refill;

determining that the prescription to refill is currently refillable; and effectuating the prescription refill task, using the virtual assistant, by communicating with a medical management system.

18. The computing system of claim 17, further comprising:

interfacing the virtual assistant with the hospital bed within the hospital room.

19. The computing system of claim 18, wherein interfacing the virtual assistant with the hospital bed within the hospital room includes:

enabling functionality on the virtual assistant to effectuate cloud-based communication between the virtual assistant and the hospital bed within the hospital room.

20. The computing system of claim 17, wherein monitoring the diction of the patient within the hospital room includes:

monitoring the diction of the patient within the hospital room to listen for utterance of a wake-up word.

21. The computing system of claim 17, wherein processing the at least a portion of the diction to identify the at least one bed-control-command to be performed on the hospital bed within the hospital room includes:

processing the at least a portion of the diction on a cloud-based computing resource to identify at least one bed-control-command to be performed on the hospital bed within the hospital room.

22. The computing system of claim 17, wherein the at least one bed-control-command to be performed on the hospital bed within the hospital room includes one or more of:

a head raise/lower bed-control-command;
a knee raise/lower bed-control-command;
a feet raise/lower bed-control-command;
a bed raise/lower bed-control-command; and
a heater on/off bed-control-command.

23. The computing system of claim 17, wherein processing the at least a portion of the diction to identify the at least one supplemental command to be performed within the hospital room includes:

processing the at least a portion of the diction on a cloud-based computing resource to identify the at least one supplemental command to be performed within the hospital room.

24. The computing system of claim 17, wherein the at least one supplemental command to be performed within the hospital room includes one or more of:

placing a food/beverage order;
requesting medication;
contacting a nurse's station;
calling for emergency assistance;
controlling a room lighting system; and
controlling a television.

* * * * *